US008288415B2

(12) United States Patent
Muller et al.

(10) Patent No.: US 8,288,415 B2
(45) Date of Patent: *Oct. 16, 2012

(54) PHARMACEUTICAL COMPOSITIONS OF 3-(4-AMINO-1-OXOISOINDOLIN-2YL)-PIPERIDINE-2,6-DIONE

(75) Inventors: George W. Muller, Bridgewater, NJ (US); David I. Stirling, Branchburg, NJ (US); Roger Shen-Chu Chen, Edison, NJ (US)

(73) Assignee: Celgene Corporation, Summit, NJ (US)

( * ) Notice: Subject to any disclaimer, the term of this patent is extended or adjusted under 35 U.S.C. 154(b) by 257 days.

This patent is subject to a terminal disclaimer.

(21) Appl. No.: 12/635,637

(22) Filed: Dec. 10, 2009

(65) Prior Publication Data

US 2010/0093799 A1   Apr. 15, 2010

Related U.S. Application Data

(60) Continuation of application No. 11/401,862, filed on Apr. 12, 2006, which is a division of application No. 10/337,602, filed on Jan. 6, 2003, now Pat. No. 7,119,106, which is a continuation of application No. 09/781,179, filed on Feb. 12, 2001, now Pat. No. 6,555,554, which is a continuation of application No. 09/543,809, filed on Apr. 6, 2000, now Pat. No. 6,281,230, which is a division of application No. 09/230,389, filed on May 7, 1999, now abandoned.

(51) Int. Cl.
*A61K 31/445* (2006.01)
*C07D 401/04* (2006.01)

(52) U.S. Cl. .................. 514/323; 546/201
(58) Field of Classification Search .......... 514/323; 546/201

See application file for complete search history.

(56) References Cited

U.S. PATENT DOCUMENTS

| | | | |
|---|---|---|---|
| 4,590,189 A | 5/1986 | Hiraga et al. | |
| 4,808,402 A | 2/1989 | Leibovich et al. | |
| 4,849,441 A | 7/1989 | Okazaki et al. | |
| 5,385,901 A | 1/1995 | Kaplan et al. | |
| 5,463,063 A | 10/1995 | Muller | |
| 5,502,066 A | 3/1996 | Heinemann et al. | |
| 5,593,990 A | 1/1997 | D'Amato | |
| 5,605,914 A | 2/1997 | Muller | |
| 5,629,327 A | 5/1997 | D'Amato | |
| 5,635,517 A * | 6/1997 | Muller et al. .................. 514/323 |
| 5,658,940 A | 8/1997 | Muller et al. | |
| 5,698,579 A | 12/1997 | Muller | |
| 5,703,098 A | 12/1997 | Muller et al. | |
| 5,712,291 A | 1/1998 | D'Amato | |
| 5,728,845 A | 3/1998 | Muller et al. | |
| 5,736,570 A | 4/1998 | Muller et al. | |
| 5,798,368 A | 8/1998 | Muller et al. | |
| 5,801,195 A | 9/1998 | Muller et al. | |
| 5,874,448 A | 2/1999 | Muller et al. | |
| 5,877,200 A | 3/1999 | Muller | |
| 5,635,517 A | 6/1999 | Muller et al. | |
| 5,929,117 A | 7/1999 | Muller et al. | |
| 5,955,476 A | 9/1999 | Muller et al. | |
| 5,968,945 A | 10/1999 | Muller et al. | |
| 6,011,050 A | 1/2000 | Muller et al. | |
| 6,020,358 A | 2/2000 | Muller et al. | |
| 6,046,221 A | 4/2000 | Muller et al. | |
| 6,071,948 A | 6/2000 | D'Amato | |
| 6,114,355 A | 9/2000 | D'Amato | |
| 6,124,322 A | 9/2000 | Bjoerkman et al. | |
| 6,214,857 B1 | 4/2001 | Muller et al. | |
| 6,228,879 B1 | 5/2001 | Green et al. | |
| 6,235,756 B1 | 5/2001 | D'Amato | |
| 6,281,230 B1 | 8/2001 | Muller et al. | |
| 6,316,471 B1 | 11/2001 | Muller et al. | |
| 6,335,349 B1 | 1/2002 | Muller et al. | |
| 6,358,945 B1 | 3/2002 | Breitfelder et al. | |
| 6,380,239 B1 | 4/2002 | Muller et al. | |
| 6,395,754 B1 | 5/2002 | Muller et al. | |
| 6,403,613 B1 | 6/2002 | Man et al. | |
| 6,420,414 B1 | 7/2002 | D'Amato | |
| 6,458,810 B1 | 10/2002 | Muller et al. | |
| 6,469,045 B1 | 10/2002 | D'Amato | |
| 6,476,052 B1 | 11/2002 | Muller et al. | |
| 6,500,845 B1 | 12/2002 | Zimmer et al. | |
| 6,518,298 B2 | 2/2003 | Green et al. | |
| 6,555,554 B2 * | 4/2003 | Muller et al. .................. 514/323 |
| 6,673,828 B1 | 1/2004 | Green et al. | |
| 6,762,195 B2 | 7/2004 | Muller et al. | |
| 6,977,268 B2 | 12/2005 | D'Amato | |
| 7,041,680 B2 | 5/2006 | Muller et al. | |
| 7,119,106 B2 * | 10/2006 | Muller et al. .................. 514/323 |
| 7,189,740 B2 | 3/2007 | Zeldis | |

(Continued)

FOREIGN PATENT DOCUMENTS

EP   0688771   12/1995

(Continued)

OTHER PUBLICATIONS

Contino-Pepin et al. "Preliminary biological . . . " Bioorg. Med. Chem. Lett. 19, p. 878-881 (2009).*
Al-Soud et al., "Synthesis and antitumor activity of some phthalimide analogues", Pharmazie 56(5), pp. 372-275 (2001).
Baker Botts, "In print-reach through claims", Attorney's Practice Profiles News and Events (2002).
Bauer et al., "Inhibition of angiogenesis by thalidomide requires metabolic activation, which is species-dependent", Biochem. Pharmacol. 55(11), pp. 1827-1834 (1998).
Bazzoli et al., "The effects of thalidomide and two analogues on the regenerating forelimb of the newt", J. Embryol. Exp. Morph. 41, pp. 125-135 (1977).
Benjamin et al., "A simple on-pot . . ." CA 2003, p. 522224 (2003).
Boylen et al., "Teratogenic effects of thalidomide and its metabolites on the developing chick enbryo", Canadian J. of Biochem., 42 (1964).

(Continued)

*Primary Examiner* — Celia Chang

(74) *Attorney, Agent, or Firm* — Jones Day

(57) ABSTRACT

Substituted 2-(2,6-dioxopiperidin-3-yl)phthalimides and 1-oxo-2-(2,6-dioxopiperidin-3-yl)isoindolines are disclosed. The compounds are useful, for example, in reducing the levels of TNFα in a mammal.

6 Claims, No Drawings

U.S. PATENT DOCUMENTS

| | | | |
|---|---|---|---|
| 7,323,479 B2 | 1/2008 | Zeldis | |
| 7,459,466 B2 | 12/2008 | Muller et al. | |
| 7,563,810 B2 * | 7/2009 | Zeldis | 514/323 |
| 7,629,360 B2 | 12/2009 | Muller et al. | |
| 7,709,502 B2 * | 5/2010 | Muller et al. | 514/323 |
| 2001/0056113 A1 | 12/2001 | D'Amato | |
| 2001/0056114 A1 | 12/2001 | D'Amato | |
| 2002/0045643 A1 | 4/2002 | Muller et al. | |
| 2002/0049231 A1 | 4/2002 | D'Amato | |
| 2002/0052398 A1 | 5/2002 | D'Amato | |
| 2002/0054899 A1 | 5/2002 | Zeldis | |
| 2002/0061911 A1 | 5/2002 | D'Amato | |
| 2002/0061923 A1 | 5/2002 | D'Amato | |
| 2002/0082290 A1 | 6/2002 | D'Amato | |
| 2002/0161023 A1 | 10/2002 | D'Amato | |
| 2002/0173658 A1 | 11/2002 | Muller et al. | |
| 2002/0183360 A1 | 12/2002 | Muller et al. | |
| 2003/0028028 A1 | 2/2003 | Man et al. | |
| 2003/0045552 A1 | 3/2003 | Robarge et al. | |
| 2003/0069428 A1 | 4/2003 | Muller et al. | |
| 2003/0096841 A1 | 5/2003 | Robarge | |
| 2003/0139451 A1 | 7/2003 | Shah et al. | |
| 2003/0144325 A1 | 7/2003 | Muller et al. | |
| 2003/0181428 A1 | 9/2003 | Green et al. | |
| 2003/0187024 A1 | 10/2003 | D'Amato | |
| 2003/0191098 A1 | 10/2003 | D'Amato | |
| 2003/0235909 A1 | 12/2003 | Hariri et al. | |
| 2004/0029832 A1 | 2/2004 | Zeldis | |
| 2004/0077685 A1 | 4/2004 | Figg et al. | |
| 2004/0077686 A1 | 4/2004 | Dannenberg et al. | |
| 2004/0087546 A1 | 5/2004 | Zeldis | |
| 2004/0091455 A1 | 5/2004 | Zeldis | |
| 2004/0122052 A1 | 6/2004 | Muller et al. | |
| 2004/0127545 A1 | 7/2004 | D'Amato et al. | |
| 2004/0147558 A1 | 7/2004 | Treston et al. | |
| 2004/0220144 A1 | 11/2004 | Zeldis | |
| 2005/0096351 A1 | 5/2005 | Jaworsky et al. | |
| 2005/0100529 A1 | 5/2005 | Zeldis | |
| 2005/0143344 A1 | 6/2005 | Zeldis et al. | |
| 2005/0143420 A1 | 6/2005 | Moutouh-de Parseval et al. | |
| 2005/0203142 A1 | 9/2005 | Zeldis et al. | |
| 2005/0214328 A1 | 9/2005 | Zeldis et al. | |
| 2005/0222209 A1 | 10/2005 | Zeldis et al. | |
| 2006/0052609 A1 | 3/2006 | Muller et al. | |

FOREIGN PATENT DOCUMENTS

| | | |
|---|---|---|
| GB | 768821 | 2/1957 |
| WO | WO 90/08128 | 7/1990 |
| WO | WO 94/20085 | 9/1994 |
| WO | WO 95/01348 | 1/1995 |
| WO | WO 97/45117 | 12/1997 |
| WO | WO 98/03502 | 1/1998 |
| WO | WO 98/19649 | 5/1998 |
| WO | WO 98/54170 | 12/1998 |
| WO | WO 01/43743 | 6/2001 |
| WO | WO 02/059106 | 8/2002 |
| WO | WO 02/064083 | 8/2002 |
| WO | WO 02/070480 | 9/2002 |
| WO | WO 92/14455 | 9/2002 |
| WO | WO 92/18496 | 10/2002 |
| WO | WO 03/014315 | 2/2003 |
| WO | WO 03/086373 | 10/2003 |
| WO | WO 03/097052 | 11/2003 |
| WO | WO 2004/035064 | 4/2004 |
| WO | WO 2004/037199 | 5/2004 |
| WO | WO 2004/041190 | 5/2004 |
| WO | WO 2004/043377 | 5/2004 |
| WO | WO 2004/043464 | 5/2004 |
| WO | WO 2004/103274 | 12/2004 |
| WO | WO 2005/023192 | 3/2005 |
| WO | WO 2005/044178 | 5/2005 |
| WO | WO 2005/044259 | 5/2005 |
| WO | WO 2005/046318 | 5/2005 |
| WO | WO 2005/065455 | 7/2005 |
| WO | WO 2005/097125 | 10/2005 |
| WO | WO 2006/091991 | 10/2005 |
| WO | WO 2005/105088 | 11/2005 |
| WO | WO 2005/110408 | 11/2005 |
| WO | WO 2005/112928 | 12/2005 |

OTHER PUBLICATIONS

Buelens, "Treatment of a grade II astrocytoma with thalidomide", Arzneimittel-forschung, 17, pp. 646-648 (1967).
Bundgaard, "Design of prodrugs", Elsevier, p. 24-25 (1985).
Burger's Medicinal Chemistry and Drug Discovery, 172-178, 949-982, Manfred Wolff ed., 5th ed. (1995).
Colville-Nash et al., "Angiogenesis and rheumathoid arthritis: pathogenic and therapeutic implications", Ann. Rheum. Dis., 51(7), pp. 919-25 (1992).
Corral et al., "Differential cytokine modulation and T cell activation by two distinct classes of thaldomide analogues that are potent inhibitors of TNF-alpha 1", The Journal of Immunology. pp. 380-386 (1999).
Corral et al., "Immunomodulation by thalidomide and thalidomide analogues", Annals of the Rheumatic Diseases 58(Suppl. 1), pp. 1107-1113 (1999).
Corral et al., "Selection of novel analogs of thalidomide with enhanced tumor necrosis factor alpha inhibitory activity", Molecular Medicine 2(4), pp. 508-515 (1996).
Craig et al., "Abcolute configuration of the enantiomers of 7-Chloro-4-[[4-diethylamino)-1-methylbutylamino] quinoline (chloroquine)", J. Org. Chem. 5, pp. 1167-1170 (1988).
Craig et al., "Potential anticancer agents. III. 2-phthalimidoaldehydes and derivatives", Potential anticancer agents, III 10, pp. 1071-1073 (1967).
D'Amato et al., "Mechanism of action of thalidomide and 3-aminothalidomide in multiple myeloma", Semin. Oncol. 28, pp. 597-601 (2001).
D'Amato et al., "S-3-aminophathalimido-glutarimide . . .", Cancer Res. 62(8), pp. 2300-2305 (2002).
D'Amato et al., "Thalidomide is an inhibitor of angiogenesis", Proc. Natl. Acad. Sci. 91, pp. 4082-4085 (1994).
De et al., "Hansch analysis for some antineoplastic glutarimides", J. Indian Chem. Soc. I.III, pp. 825-826 (1976).
De et al., "Possible antineoplastic agents I", J. Pharm. Sci. 64(2), pp. 262-266 (1975).
De et al., "Possible antineoplastic agents II", J. Pharm. Sci. 66(2), pp. 232-235 (1977).
De et al., "Possible antineoplastic agents III. Synthesis of 6-alkyl-2[4'-methoxyphthalimido] and 6-alkyl-3-[3'-4'-dimethoxyphenyl] glutarimides", J. Indian Chem. Soc. I.III, pp. 1122-1125 (1976).
De et al., "Possible antineoplastic agents IV—Synthesis & antineoplastic potency of N-substituted a-(4,5-dime thoxy phthalimido)glutarimides & B-(4-bromo phenyl)glutarimides", Indian Jour. Chem. 16B, pp. 510-512 (1978).
De et al., "Quantitative structure-activity relationship (QSAR) and rational drug design for some antineoplastic thalidomide and glutarimide derivatives", J. Indian Chem. Soc. LIII, pp. 1049-1052 (1976).
Di Paolo, "In vitro test systems for cancer chemotherapy, II, correlation of in vitro inhibition of dehydrogenase and growth with in vivo inhibition of Ehrlich ascites tumor", P.S.E.B.M. 114, pp. 384-387 (1963).
Fabro et al., "Teratogenic activity of thalidomide and related compounds", Life Sciences, 3, pp. 987-992 (1964).
Feiser, Experiments in Organic Chemistry, 3rd Edition, p. 75 (1955).
Fickentscher et al., "Sterechemical properties and teratogenic activity of some tetrahydrophthalimides", Molecular Pharmacology 13, pp. 133-141 (1977).
Folkman et at., "Angiogenesis", J. Biol. Chem., 267(16), pp. 10931-10934 (1992).
Gelato et al., "Inhibition of prolactin release by a thalidomide-related compound", P.S.E.B.M. 114, pp. 167-168 (1972).
Gershbein, "The thalidomide analog, EM 12, enhances 1,2-dimethylhydrazine-induction of rat colon adnocarcinomas", Cancer Letters 60, pp. 129-133 (1991).
Gordon et al., "Thalidomide in the treatment . . .", Gut 54, pp. 540-545 (2004).

Gordon et al., "Thalidomide teratogenesis: evidence for a toxic arene oxide metabolite", Proc. Natl. Acad. Sci. USA 78(4), pp. 2545-2548 (1981).

Grabstald et al., "Clinical experiences with thalidomide in patients with cancer", Clinical Pharmacology and Therapeutics 6, pp. 298-302 (1965).

Hastings, "Kellersberger Memorial Lecture 1979: Immunosuppressive/anti-inflammatory thalidomide analogues", Ethiop. Med. J. 18, p. 65-71 (1980).

He et al., "Synthesis of thalidomide analogs and their biological potential for treatment of Graft Versus Host Disease (GVHD)", a full article of J. Am. Chem. Soc., Abstract 216 (1993).

Heger et al., "Enbryotoxic effects . . .", CA 110, p. 33610 (1989).

Helm et al., "Comparative teratological investigation of compounds structurally and pharmacologically related to thalidomide", Arzneim Forsch. Drug Res.31(I) 6, pp. 941-949 (1981).

Hellman, "Prolongation of skin homograft survival by thalidomide", Brit. Med. J. 2, pp. 687-689 (1965).

Jonsson, "Chemical structure and teratogenic properties", Acta Pharma. Succica 9, pp. 431-436 (1972).

Jonsson, "Chemical structure and teratogenic properties. A review of available data on structure-activity relationships and mechanism of action of thalidomide analogues", Acta Pharma. Succica 9, pp. 521-542 (1972).

Jonsson, "Chemical structure and teratogenic properties. A review of available data on structure-activity relationships and mechanism of action of thalidomide analogues", Acta Pharma. Succica 9, pp. 543-562 (1972).

Kamoshida et al., "Expression of cancer . . . ", Biomed. Res. 27, pp. 275-281 (2006).

Koch, "Thalidomide and congeners as anti-inflammatory agents", Medicinal Chemistry 22, pp. 166-242 (1985).

Koch, "The arene oxide hypothesis of thalidomide action: considerations on the molecular mechanism of action of the classical teratogen", Sci. Pharm. 49, pp. 67-99 (1981).

Lendaris et al., "Reach through claims . . . ", Intellectual Property Update 4(5) (2004).

Lentzsch et al., "S-3-aminophthalimido-glutarimide inhibits angiogenesis and growth of B-cell neoplasias in mice", Cancer Research, 62, pp. 2300-2305 (2002).

Luzzio et al., "Synthesis and antiangiogenic activity of 2-deoxygenerated analogs and 6'-deoxygenated metabolic analogs of thalidomide", MEDI, Abstract No. 185.

LU7710 et al., "Thalidomide analogues . . . ", Exp. Opinion ther. Patents 1492, pp. 215-229 (2004).

Menard et al., "Quelques metabolites possibles de la thalidomide", Canadian J. Chem., 41, pp. 1722-1725 (1963).

Miyachi et al., "Enantio-dependence of inducer-specific bidirectional regulation of tumor necrosis factor (TNF)-alpha production: potent TNF-alpha production inhibitors", Bioorg. Med. Chem. Letter 6(19), p. 2293 (1996).

Miyachi et al., "Novel biological response modifiers: phthalimides with tumor necrosis factor-alpha production regulating activity", J. Med. Chem. 40, pp. 2858-2865 (1997).

Miyachi et al., "Tumor necrosis factor-alpha production enhancing activity of substituted 3'-methylthalidomide: influence of substitutes at the phthaloyl moiety on the activity of steroselectivity", Chem. Pharm. Bull. 46(7), pp. 1165-1168 (1998).

Muckter, "Thalidomide and tumor," Antimicrobial Agents and Chemotherapy, 531-538 (1965).

Muller et al., "Amino-substituted thalidomide analogs: potent inhibitors of Tnf-production", Bioorganic & Medicinal Chem. Letters 9, pp. 1625-1630 (1999).

Muller et al., "Structural modifications of thalidomide produce analogs with enhanced tumor necrosis factor inhibitory activity", Journal of Medicinal Chemistry 39(17), pp. 3238-3240 (1996).

Muller et al., "Thalidomide analogs and PDE4 inhibition", Bioorganic & Medicinal Chemistry Letters 8, pp. 2669-2674 (1998).

Naik et al., "The hydrolysis of . . . ", CA 118, p. 131893 (1993).

Nishimura et al., "S-form of methyln-phthalimidoglutaimide but not its (R)-form, enhanced phorbol ester-induced TNF alpha production by human leukemia cell HL-60: implication of optical resolution of thalilomidal effect", Chem. Pharm. Bull. 42(5), p. 1157 (1994).

Nishimura et al., "S-form of methyln-phthalimidoglutaimide", CA 121:73088 (1994).

Niwayama et al., "Enhanced potency of perfluorinated thalidomide derivatives for inhibition of LPS-induced tumor necrosis factor-Production is associated with a change of mechanism of action", Bioorganic & Medicinal Chemistry Letters 7, pp. 1071-1076 (1998).

Niwayama et al., "Potent inhibition of tumor necrosis factor-production by tetrafluorothalidomide and trtrylfluorophtalimides", J. Med. Chem., pp. 3044-3045 (1996).

Niwayama et al., "Potent inhibition of tumor necrosis factor alpha production . . . ", CA 125, p. 104270, (1996).

Olson et al., "Thalidomide (N-phthaloylglutamimide) in the treatment of advanced cancer", Clinical Pharmacology and Therapeutics 6(3), pp. 292-297 (1965).

Schmahl et al., Arch. Toxicol. 70(11), pp. 749-756 (1996).

Schmahl et al., "Stereoselective distribution of . . . ", CA 110, p. 822 (1989).

Schmahl et al., "Stereoselective distribution of . . . ", CA 126, p. 1148 (1996).

Schumacher et al., "The metabolism of thalidomide: the fate of thalidomide and some of its hydrolysis products in various species", Brit. J. Pharmacol. 25, pp. 338-351 (1965).

Schweigerer et al., "Angiogenesis and angiogenesis inhibitors in pediatric diseases", Eur. J. Pediatrics 151, pp. 472-476 (1992).

Sekut et al., Pathophysiology and regulation of TNF-a in inflammation, DN&P. 9(5), pp. 261-269 (1996).

Sampaio et al., "Thalidomide selectively inhibits tumor necrosis factor alpha production by stimulated human monocytes", J. Exp. Med., The Rockefeller University Press 173, pp. 699-703 (1991).

Shah et al., "Synthesis and enantiomeric separation of 2-phthalimidino-glutaric acid analogues: potent inhibitors of tumor metastasis", J. Med. Chem. 42, pp. 3014-3017 (1999).

Shannon et al., "Immunomodulatory assays to study structure-activity relationships of thalidomide", Immunopharmacology 35, pp. 203-212 (1997).

Shibata et al., "N-alkylphthalimides: structural requirement of thalimidomidal action on 12-0-tetradecanoylphorbol-13-acetate-induced tumor necrosis factor a production by human leukemia HL-60 cells", Chem. Pharm. Bull. 43(1), pp. 177-179 (1995).

Shimazawa et al., "Antiangiogenic activity of tumor necrosis factor-alpha production regulators derived from thalidomide", Biol. Pharm. Bull. 22(2), pp. 224-226 (1999).

Smith et al., "Studies on the relationship between the chemical structure and embryotoxic activity of thalidomide and related compounds", A Symposium on Embryopathic Activity of Drugs, London, pp. 194-209 (1965).

Suaer et al., "Thalidomide inhibits angiogenesis in embryoid bodies by the generation of hydroxyl radicals", Am. J. Pathol. 156(1), pp. 151-158 (2000).

Sugiura et at., "Effects of thalidomide on transplantable mouse, rat, and hamster tumors", GANN 55, pp. 57-60 (1964).

Takeuchi et al., (R)- and (S)-3-fluorothalidomides: isosteric analogues of thalidomide, American Chemical Society 1(10), pp. 1571-1573 (1999).

Torry et al., "Angiogenesis in the uterus: potential regulation and relation to tumor angiogenesis", Am. J. Reproductive Immunol. 27, pp. 171-179 (1992).

Traldi, et al., "L'impiego dell'imide dell'acido N-ftalilglutammico (talidomide) nella terapia sintomatica del vomito di molti pazienti da neoplasie maligne o causato della somministrazione di cloridato di mecloretamina", Cancro 18, pp. 336-341 (1965).

Trilaterao Project B3b, "Comparative study on reach through claims", Introduction (2001).

Udagawa et al., "Thalidomides and analogs", Antiangiogenic Agents in Cancer Therapy, Humana Press, Totowa, NJ, pp. 263-274 (1998).

Wnendt et al., "Enantioselective inhibition of . . . ", CA 126, p. 387 (1996).

Wnendt et al., "Enantioselective inhibition of TNF-alpha release by thalidomide and thalidomide-analogues", Chilality 8, pp. 390-396 (1996).

Yeh et al., "Geriatric cachexia . . . ", Am. J. Clin. Nutr. 70, pp. 183-197 (1999).

Zwingenberger et al., "Immunomodulation by thalidomide: systematic review of the literature and of unpublished observations", Journal of Inflammation, pp. 177-211 (1996).

U.S. Appl. No. 09/287,377 filed Apr. 7, 1999 (D'Amato).

U.S. Appl. No. 09/545,654 filed Apr. 10, 2000 (D'Amato).

U.S. Appl. No. 10/003,461 filed Nov. 30, 2001 (Treston et al.).

U.S. Appl. No. 60/048,278 filed May 30, 1997 (Muller).

USPTO, U.S. Appl. No. 11/401,862, Non-Final Office Action mailed Jul. 9, 2009.

USPTO, U.S. Appl. No. 11/401,862, Non-Final Office Action mailed Jun. 5, 2008.

USPTO, U.S. Appl. No. 11/401,858, Advisory Action mailed Jun. 24, 2009.

USPTO, U.S. Appl. No. 11/401,858, Final Office Action mailed Mar. 11, 2009.

USPTO, U.S. Appl. No. 11/401,858, Non-Final Office Action mailed Jul. 2, 2008.

Notification letter dated Aug. 30, 2010 from Natco Pharma Limited to Celgene Corporation re: Notification pursuant to § 505(j)(2)(B) of the Federal Food, Drug and Cosmetic Act.

Grosshans et al., "Thalidomide Therapy for Inflammatory Dermatoses", International Journal of Dermatology, 23: 598-602 (1984).

Krenn et al., "Improvements in Solubility and Stability of Thalidomide upon Complexation with Hydropropy1-β-Cyclodextrin", Journal of Pharmaceutical Sciences, 81(7): 685-689 (1992).

Schmahl et al., "Pharmacokinetics of the Teratogenic and Nonteratogenic Thalidomide Analogs EM12 and Supidimide in the Rat and Marmoset Monkey", in Pharmacokinetics in Teratogenesis, vol. I, CRC Press, pp. 181-192 (1987).

Schumacher et al., "The Teratogenic Activity of a Thalidomide Analogue, EM12, in Rabbits, Rats, and Monkeys", Teratology, 5: 233-240 (1971).

* cited by examiner

PHARMACEUTICAL COMPOSITIONS OF 3-(4-AMINO-1-OXOISOINDOLIN-2YL)-PIPERIDINE-2,6-DIONE

This is a continuation of co-pending U.S. application Ser. No. 11/401,862, filed Apr. 12, 2006, which is a division of U.S. application Ser. No. 10/337,602, filed Jan. 6, 2003, now U.S. Pat. No. 7,119,106, which is a continuation of U.S. application Ser. No. 09/781,179, filed Feb. 12, 2001, now U.S. Pat. No. 6,555,554, which is a continuation of U.S. application Ser. No. 09/543,809, filed Apr. 6, 2000, now U.S. Pat. No. 6,281,230, which is a division of U.S. application Ser. No. 09/230,389, filed May 7, 1999, now abandoned, which is based on application no. PCT/US97/13375, filed Jul. 24, 1997, which claims the benefit of U.S. application Ser. Nos. 08/690,258, filed Jul. 24, 1996, now U.S. Pat. Nos. 5,635,517 and 08/701,494, filed Aug. 22, 1996, now U.S. Pat. No. 5,798,368, and of U.S. provisional application No. 60/048,278, filed May 30, 1997, all of which are incorporated herein in their entireties by reference.

The present invention relates to substituted 2-(2,6-dioxopiperidin-3-yl)phthalimides and substituted 2-(2,6-dioxopiperidin-3-yl)-1-oxoisoindolines, the method of reducing levels of tumor necrosis factor α in a mammal through the administration thereof, and pharmaceutical compositions of such derivatives.

BACKGROUND OF THE INVENTION

Tumor necrosis factor α, or TNFα, is a cytokine which is released primarily by mononuclear phagocytes in response to a number immunostimulators. When administered to animals or humans, it causes inflammation, fever, cardiovascular effects, hemorrhage, coagulation, and acute phase responses similar to those seen during acute infections and shock states. Excessive or unregulated TNFα production thus has been implicated in a number of disease conditions. These include endo-toxemia and/or toxic shock syndrome {Tracey et al., Nature 330, 662-664 (1987) and Hinshaw et al., Circ. Shock 30, 279-292 (1990)}; cachexia {Dezube et al., Lancet, 335 (8690), 662 (1990)} and Adult Respiratory Distress Syndrome where TNFα concentration in excess of 12,000 pg/mL have been detected in pulmonary aspirates from ARDS patients {Millar et al., Lancet 2(8665), 712-714 (1989)}. Systemic infusion of recombinant TNFα also resulted in changes typically seen in ARDS {Ferrai-Baliviera et al., Arch. Surg. 124(12), 1400-1405 (1989)}.

TNFα appears to be involved in bone resorption diseases, including arthritis. When activated, leukocytes will produce bone-resorption, an activity to which the data suggest TNFα contributes. {Bertolini et al., Nature 319, 516-518 (1986) and Johnson et al., Endocrinology 124(3), 1424-1427 (1989).} TNFα also has been shown to stimulate bone resorption and inhibit bone formation in vitro and in vivo through stimulation of osteoclast formation and activation combined with inhibition of osteoblast function. Although TNFα may be involved in many bone resorption diseases, including arthritis, the most compelling link with disease is the association between production of TNFα by tumor or host tissues and malignancy associated hypercalcemia {Calci. Tissue Int. (US) 46(Suppl.), S3-10 (1990)}. In Graft versus Host Reaction, increased serum TNFα levels have been associated with major complication following acute allogenic bone marrow transplants {Holler et al., Blood, 75(4), 1011-1016 (1990)}.

Cerebral malaria is a lethal hyperacute neurological syndrome associated with high blood levels of TNFα and the most severe complication occurring in malaria patients. Levels of serum TNFα correlated directly with the severity of disease and the prognosis in patients with acute malaria attacks {Grau a al., N. Engl. J. Med. 320(24), 1586-1591 (1989)}.

Macrophage-induced angiogenesis TNFα is known to be mediated by TNFα. Leibovich et al. {Nature, 329, 630-632 (1987)} showed TNFα induces in vivo capillary blood vessel formation in the rat cornea and the developing chick chorioallantoic membranes at very low doses and suggest TNFα is a candidate for inducing angiogenesis in inflammation, wound repair, and tumor growth. TNFα production also has been associated with cancerous conditions, particularly induced tumors {Ching et al., Brit. J. Cancer, (1955) 72, 339-343, and Koch, Progress in Medicinal Chemistry, 22, 166-242 (1985)}.

TNFα also plays a role in the area of chronic pulmonary inflammatory diseases. The deposition of silica particles leads to silicosis, a disease of progressive respiratory failure caused by a fibrotic reaction. Antibody to TNFα completely blocked the silica-induced lung fibrosis in mice {Pignet et al., Nature, 344:245-247 (1990)}. High levels of TNFα production (in the scrum and in isolated macrophages) have been demonstrated in animal models of silica and asbestos induced fibrosis {Bissonnette et al., Inflammation 13(3), 329-339 (1989)}. Alveolar macrophages from pulmonary sarcoidosis patients have also been found to spontaneously release massive quantities of TNFα as compared with macrophages from normal donors {Baughman et al., J. Lab. Clin. Med. 115(1), 36-42 (1990)}.

TNFα is also implicated in the inflammatory response which follows reperfusion, called reperfusion injury, and is a major cause of tissue damage after loss of blood flow {Vedder et al., PNAS 87, 2643-2646 (1990)}. TNFα also alters the properties of endothelial cells and has various pro-coagulant activities, such as producing an increase in tissue factor pro-coagulant activity and suppression of the anticoagulant protein C pathway as well as down-regulating the expression of thrombomodulin {Sherry et al., J. Cell Biol. 107, 1269-1277 (1988)}. TNFα has pro-inflammatory activities which together with its early production (during the initial stage of an inflammatory event) make it a likely mediator of tissue injury in several important disorders including but not limited to, myocardial infarction, stroke and circulatory shock. Of specific importance may be TNFα-induced expression of adhesion molecules, such as intercellular adhesion molecule (ICAM) or endothelial leukocyte adhesion molecule (ELAM) on endothelial cells {Munro et al., Am. J. Path. 135(1), 121-132 (1989)}.

TNFα blockage with monoclonal anti-TNFα antibodies has been shown to be beneficial in rheumatoid arthritis {Elliot et al., Int. J. Pharmac. 1995 17(2), 141-145} and Crohn's disease {von Dullemen et al., Gastroenterology, 1995 109(1), 129-135}

Moreover, it now is known that TNFα is a potent activator of retrovirus replication including activation of HIV-1. {Duh et al., Proc. Nat. Acad. Sci. 86, 5974-5978 (1989); Poll et al., Proc. Nat. Acad. Sci. 87, 782-785 (1990); Monto et al., Blood 79, 2670 (1990); Clouse et al., J. Immunol. 142, 431-438 (1989); Poll et al., AIDS Res. Hum. Retrovirus, 191-197 (1992)}. AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Cytokines, specifically TNFα, are implicated in activated T-cell mediated HIV protein expression and/or virus replication by playing a role in maintaining T lymphocyte activation. Therefore, interference with cytokine activity such as by prevention or inhibition of cytokine production, notably TNFα, in an HIV-infected individual assists in limiting the maintenance of T lymphocyte caused by HIV infection.

Monocytes, macrophages, and related cells, such as kupffer and glial cells, also have been implicated in maintenance of the HIV infection. These cells, like T cells, are targets for viral replication and the level of viral replication is dependent upon the activation state of the cells. {Rosenberg et al., The Immunopathogenesis of HIV Infection, Advances in Immunology, 57 (1989)}. Cytokines, such as TNFα, have been shown to activate HIV replication in monocytes and/or macrophages {Poli et al., Proc. Natl. Acad. Sci., 87, 782-784 (1990)}, therefore, prevention or inhibition of cytokine production or activity aids in limiting HIV progression for T cells. Additional studies have identified TNFα as a common factor in the activation of HIV in vitro and has provided a clear mechanism of action via a nuclear regulatory protein found in the cytoplasm of cells (Osborn, et al., PNAS 86 2336-2340). This evidence suggests that a reduction of TNFα synthesis may have an antiviral effect in HIV infections, by reducing the transcription and thus virus production.

AIDS viral replication of latent HIV in T cell and macrophage lines can be induced by TNFα {Folks et al., PNAS 86, 2365-2368 (1989)}. A molecular mechanism for the virus inducing activity is suggested by TNFα's ability to activate a gene regulatory protein (NFκB) found in the cytoplasm of cells, which promotes HIV replication through binding to a viral regulatory gene sequence (LTR) {Osborn et al., PNAS 86, 2336-2340 (1989)}. TNFα in AIDS associated cachexia is suggested by elevated serum TNFα and high levels of spontaneous TNFα production in peripheral blood monocytes from patients {Wright a al., J. Immunol. 141(1), 99-104 (1988)}. TNFα has been implicated in various roles with other viral infections, such as the cytomegalia virus (CMV), influenza virus, adenovirus, and the herpes family of viruses for similar reasons as those noted.

The nuclear factor κB (NFκB) is a pleiotropic transcriptional activator (Lenardo, et al., Cell 1989, 58, 227-29). NFκB has been implicated as a transcriptional activator in a variety of disease and inflammatory states and is thought to regulate cytokine levels including but not limited to TNFα and also to be an activator of HIV transcription (Dbaibo, et al., J. Biol. Chem. 1993, 17762-66; Duh a al., Proc. Natl. Acad. Sci. 1989, 86, 5974-78; Bachelerie et al. Nature 1991, 350, 709-12; Boswas et al., J. Acquired Immune Deficiency Syndrome 1993, 6, 778-786; Suzuki et al., Biochem. And Biophys. Res. Comm. 1993, 193, 277-83; Suzuki et al. Biochem. And Biophys. Res Comm. 1992, 189, 1709-15; Suzuki et al. Biochem. Mol. Bio. Int. 1993, 31(4), 693-700; Shakhov et al., Proc. Natl. Acad. Sci. USA 1990, 171, 35-47; and Staal et al., Proc. Natl. Acad. Sci. USA 1990, 87, 9943-47). Thus, inhibition of NFκB binding can regulate transcription of cytokine gene(s) and through this modulation and other mechanisms be useful in the inhibition of a multitude of disease states. The compounds described herein can inhibit the action of NFκB in the nucleus and thus are useful in the treatment of a variety of diseases including but not limited to rheumatoid arthritis, rheumatoid spondylitis, osteoarthritis, other arthritic conditions, septic shock, septis, endotoxic shock, graft versus host disease, wasting, Crohn's disease, ulcerative colitis, multiple sclerosis, systemic lupus erythematosis, ENL in leprosy, HIV, AIDS, and opportunistic infections in AIDS. TNFα and NFκB levels are influenced by a reciprocal feedback loop. As noted above, the compounds of the present invention affect the levels of both TNFα and NFκB.

Many cellular functions are mediated by levels of adenosine 3',5'-cyclic monophosphate (cAMP). Such cellular functions can contribute to inflammatory conditions and diseases including asthma, inflammation, and other conditions (Lowe and Cheng, Drugs of the Future, 17(9), 799-807, 1992). It has been shown that the elevation of cAMP in inflammatory leukocytes inhibits their activation and the subsequent release of inflammatory mediators, including TNFα and NFκB. Increased levels of cAMP also leads to the relaxation of airway smooth muscle.

Decreasing TNFα levels and/or increasing cAMP levels thus constitutes a valuable therapeutic strategy for the treatment of many inflammatory, infectious, immunological, and malignant diseases. These include but are not restricted to septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, oncogenic or cancerous conditions, asthma, autoimmune disease, opportunistic infections in AIDS, rheumatoid arthritis, rheumatoid spondylitis, osteoarthritis, other arthritic conditions, Crohn's disease, ulcerative colitis, multiple sclerosis, systemic lupus erythematosis, ENL in leprosy radiation damage, oncogenic conditions, and hyperoxic alveolar injury. Prior efforts directed to the suppression of the effects of TNFα have ranged from the utilization of steroids such as dexamethasone and prednisolone to the use of both polyclonal and monoclonal antibodies {Beutler et al., Science 234, 470-474 (1985); WO 92/11353}.

DETAILED DESCRIPTION

The present invention is based on the discovery that certain classes of non-polypeptide compounds more fully described herein decrease the levels of TNFα.

In particular, the invention pertains to (i) compounds of the formula:
in which:

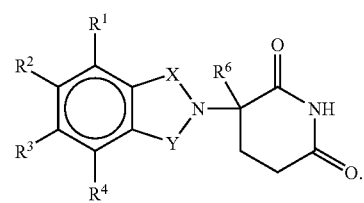

one of X and Y is C=1 and the other of X and Y is OA) or CH₂;
(i) each of R¹, R², R³, and R⁴, independently of the others, is halo, alkyl of 1 to 4 carbon atoms, or alkoxy of 1 to 4 carbon atoms or (ii) one of R¹, R², R³, and R⁴ is —NHR⁵ and the remaining of R¹, R², R³, and it are hydrogen;
R⁵ is hydrogen or alkyl of 1 to 8 carbon atoms;
R⁶ is hydrogen, alkyl of 1 to 8 carbon atoms, benzyl, or halo;

provided that $R^6$ is other than hydrogen if X and Y are C-31 and (i) each of $R^1$, $R^2$, $R^3$, and $R^4$ is fluoro or (ii) one of $R^1$, $R^2$, $R^3$, or $R^4$ is amino; and (b) the acid addition salts of said compounds which contain a nitrogen atom capable of being protonated.

A preferred group of compounds are those of Formula I in which each of $R^1$, $R^2$, $R^3$, and $R^4$, independently of the others, is halo, alkyl of 1 to 4 carbon atoms, or alkoxy of 1 to 4 carbon atoms, and $R^6$ is hydrogen, methyl, ethyl, or propyl. A second preferred group of compounds are those of Formula I in which one of $R^1$, $R^2$, $R^3$, and $R^4$ is —$NH_2$, the remaining of $R^1$, $R^2$, $R^3$, and $R^4$ are hydrogen, and $R^6$ is hydrogen, methyl, ethyl, or propyl.

Unless otherwise defined, the term alkyl denotes a univalent saturated branched or straight hydrocarbon chain containing from 1 to 8 carbon atoms. Representative of such alkyl groups are methyl, ethyl, propyl, isopropyl, butyl, isobutyl, sec-butyl, and tert-butyl. Alkoxy refers to an alkyl group bound to the remainder of the molecule through an ethereal oxygen atom. Representative of such alkoxy groups are methoxy, ethoxy, propoxy, isopropoxy, butoxy, isobutoxy, sec-butoxy, and tert-butoxy. Preferably $R^1$, $R^2$, $R^3$, and $R^4$ are chloro, fluoro, methyl or methoxy.

The compounds of Formula I are used, under the supervision of qualified professionals, to inhibit the undesirable effects of TNFα. The compounds can be administered orally, rectally, or parenterally, alone or in combination with other therapeutic agents including antibiotics, steroids, etc., to a mammal in need of treatment.

The compounds of the present invention also can be used topically in the treatment or prophylaxis of topical disease states mediated or exacerbated by excessive TNFα production, respectively, such as viral infections, such as those caused by the herpes viruses, or viral conjunctivitis, psoriasis, atopic dermatitis, etc.

The compounds also can be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anaemia virus, caprine arthritis virus, visna virus, and maedi virus, as well as other lentiviruses.

Compounds in which one of $R^1$, $R^2$, $R^3$, $R^4$ is amino and $R^5$ and $R^6$, as well as the remainder of $R^1$, $R^2$, $R^3$, $R^4$, are hydrogen, as for example, 1,3-dioxo-2-(2,6-dioxopiperidin-3-yl)-4-aminoisoindoline or 1,3-dioxo-2-(2,6-dioxopiperidin-3-yl)-5-aminoisoindoline are known. See, e.g., Jönsson, *Acta Pharma. Succica*, 9, 521-542 (1972).

The compounds can be prepared using methods which are known in general. In particular, the compounds can be prepared through the reaction of 2,6-dioxopiperidin-3-ammonium chloride, and a lower alkyl ester of 2-bromomethylbenzoic acid in the presence of an acid acceptor such as dimethylaminopyridine or triethylamine.

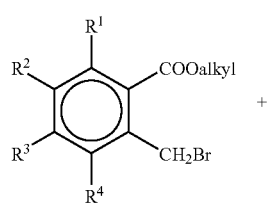

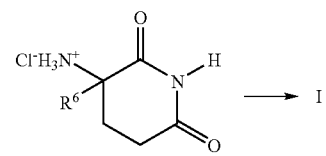

The substituted benzoate intermediates are known or can be obtained though conventional processes. For example, a lower alkyl ester of an ortho-toluic acid is brominated with N-bromosuccinimide under the influence of light to yield the lower alkyl 2-bromomethylbenzoate.

Alternatively, a dialdehyde is allowed to react with 2,6-dioxopiperidin-3-ammonium chloride:

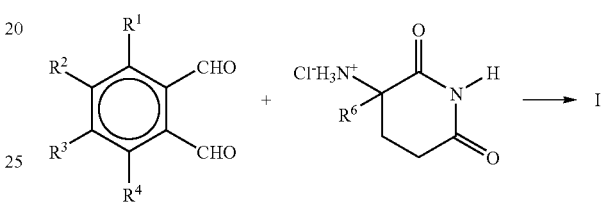

In a further method, a dialdehyde is allowed to react with glutamine and the resulting 2-(1-oxoisoindolin-2-yl)glutaric acid then cyclized to yield a 1-oxo-2-(2,6-dioxopiperidin-3-yl)-isoindoline of Formula I:

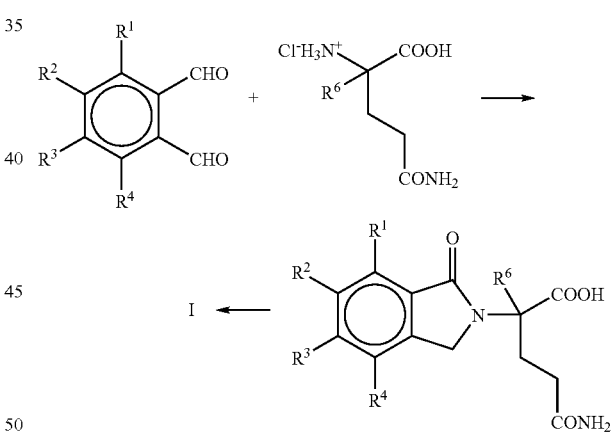

Finally, an appropriately substituted phthalidimide intermediate is selectively reduced:

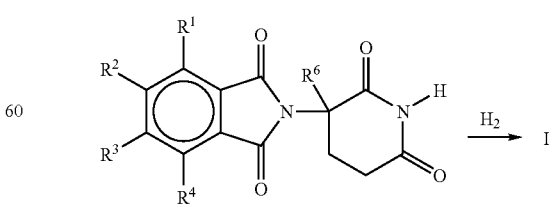

Amino compounds can be prepared through catalytic hydrogenation of the corresponding nitro compound:

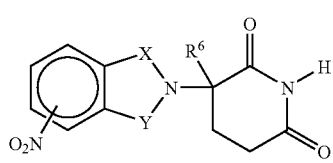

IA

The nitro intermediates of Formula IA are known or can be obtained though conventional processes. For example, a nitrophthalic anhydride is allowed to react with α-aminoglutarimide hydrochloride (alternatively named as 2,6-dioxopiperidin-3-ylammonium chloride) in the presence of sodium acetate and glacial acetic acid to yield an intermediate of Formula IA in which X and Y are both C=O.

In a second mute, a lower alkyl ester of nitro-ortho-toluic acid is brominated with N-bromosuccinimide under the influence of light to yield a lower alkyl 2-(bromomethyl)nitrobenzoate. This is allowed to react with 2,6-dioxopiperidin-3-ammonium chloride in, for example, dimethylformamide in the presence of triethylamine to yield an intermediate of Formula II in which one of X is C=O and the other is $CH_2$.

Alternatively, if one of $R_1$, $R_2$, $R_3$, and $R_4$ is protected amino, the protecting group can be cleaved to yield the corresponding compound in which one of $R_1$, $R_2$, $R_3$, and $R_4$ is amino. Protecting groups utilized herein denote groups which generally are not found in the final therapeutic compounds but which are intentionally introduced at some stage of the synthesis in order to protect groups which otherwise might be altered in the course of chemical manipulations. Such protecting groups are removed at a later stage of the synthesis and compounds bearing such protecting groups thus are of importance primarily as chemical intermediates (although some derivatives also exhibit biological activity). Accordingly the precise structure of the protecting group is not critical. Numerous reactions for the formation and removal of such protecting groups are described in a number of standard works including, for example, "Protective Groups in Organic Chemistry", Plenum Press, London and New York, 1973; Greene, Th. W. "Protective Groups in Organic Synthesis", Wiley, New York, 1981; "The Peptides", Vol. I, Schröder and Lubke, Academic Press, London and New York, 1965; "Methoden der organischen Chemie", Houben-Weyl, 4th Edition, Vol. 15/1, Georg Thieme Verlag, Stuttgart 1974, the disclosures of which are incorporated herein by reference. An amino group can be protected as an amide utilizing an acyl group which is selectively removable under mild conditions, especially benzyloxycarbonyl, formyl, or a lower alkanoyl group which is branched in 1- or α position to the carbonyl group, particularly tertiary alkanoyl such as pivaloyl, a lower alkanoyl group which is substituted in the position a to the carbonyl group, as for example trifluoroacetyl.

The compounds of the present invention possess a center of chirality and can exist as optical isomers. Both the racemates of these isomers and the individual isomers themselves, as well as diastereomers when there are two chiral centers, are within the scope of the present invention. The racemates can be used as such or can be separated into their individual isomers mechanically as by chromatography using a chiral adsorbent. Alternatively, the individual isomers can be prepared in chiral form or separated chemically from a mixture by forming salts with a chiral acid, such as the individual enantiomers of 10-camphorsulfonic acid, camphoric acid, α-bromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as obtain either or both substantially free of the other; i.e., in a form having an optical purity of >95%.

The present invention also pertains to the physiologically acceptable non-toxic acid addition salts of the compounds of Formula I. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

Oral dosage forms include tablets, capsules, dragees, and similar shaped, compressed pharmaceutical forms containing from 1 to 100 mg of drug per unit dosage. Isotonic saline solutions containing from 20 to 100 mg/mL can be used for parenteral administration which includes intramuscular, intrathecal, intravenous and intra-arterial routes of administration. Rectal administration can be effected through the use of suppositories formulated from conventional carriers such as cocoa butter.

Pharmaceutical compositions thus comprise one or more compounds of the present invention associated with at least one pharmaceutically acceptable carrier, diluent or excipient. In preparing such compositions, the active ingredients are usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

The compositions preferably are formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient. The compositions can be formulated so as to Provide an immediate, sustained or delayed release of active ingredient after administration to the patient by employing procedures well known in the art.

Oral dosage forms include tablets, capsules, dragees, and similar shaped, compressed pharmaceutical forms containing from 1 to 100 mg of drug per unit dosage. Isotonic saline solutions containing from 20 to 100 mg/mL can be used for parenteral administration which includes intramuscular, intrathecal, intravenous and intra-arterial routes of administration. Rectal administration can be effected through the use of suppositories formulated from conventional carriers such as cocoa butter.

Pharmaceutical compositions thus comprise one or more compounds of the present invention associated with at least one pharmaceutically acceptable carrier, diluent or excipient. In preparing such compositions, the active ingredients are usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

The compositions preferably are formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient.

The compositions can be formulated so as to provide an immediate, sustained or delayed release of active ingredient after administration to the patient by employing procedures well known in the art.

The following examples will serve to further typify the nature of this invention but should not be construed as a limitation in the scope thereof, which scope is defined solely by the appended claims.

Example 1

1,3-Dioxo-2-(2,6-diaxopiperidin-3-yl)-5-aminoisoindoline

A mixture of 1,3-dioxo-2-(2,6-dioxopiperidin-3-yl)-5-nitroisoindoline (alternatively named as N-(2,6-dioxopiperidin-3-yl)-4-nitrophthalimide) (1 g, 3.3 mmol) and 10% Pd/C (0.13 g) in 1,4-dioxane (200 mL) was hydrogenated at 50 psi for 6.5 hours. The catalyst was filtered through Celite and the filtrate concentrated in vacuo. The residue was crystallized from ethyl acetate (20 mL) to give 0.62 g (69%) of 1,3-dioxo-2-(2,6-dioxopiperidin-3-yl)-5-aminoisoindoline {alternatively named as N-(2,6-dioxopiperidin-3-yl)-4-aminophthalimide} as an orange solid. Recrystallization from dioxane/ethyl acetate gave 0.32 g of yellow solid: mp 318.5-320.5° C.; HPLC (nova Pak C18, I 5/85 acetonitrile/0.1% $H_3PO_4$) 3.97 min (98.22%): $^1$H NMR (DMSO-$d_6$) δ 11.08 (s, 1H), 7.53-7.50 (d, J=8.3 Hz, 1H), 6.94 (s, 1H), 6.84-6.81 (d, J=8.3 Hz, 1H), 6.55 (s, 2H), 5.05-4.98 (m, 1H), 2.87-1.99 (m, 4H); $^{13}$C NMR (DMSO-$d_6$) δ 172.79, 170.16, 167.65, 167.14, 155.23, 134.21, 125.22, 116.92, 116.17, 107.05, 48.58, 30.97, 22.22; Anal. Calcd for $C_{13}H_{11}N_3O_4$: C, 57.14; H, 4.06; N, 15.38. Found: C, 56.52; H, 4.17; N, 14.60.

In a similar fashion from 1-oxo-2-(2,6-dioxopiperidin-3-yl)-5-nitroisoindoline, 1-oxo-2-(2,6-dioxopiperidin-3-yl)-4-nitroisoindoline, 1-oxo-2-(2,6-dioxopiperidin-3-yl)-6-nitroisoindoline, 1-oxo-2-(2,6-dioxopiperidin-3-yl)-7-nitroisoindoline, and 1,3-dioxo-2-(2,6-dioxopiperidin-3-yl)-4-nitroisoindoline, there is respectively obtained 1-oxo-2-(2,6-dioxopiperidin-3-yl)-5-aminoisoindoline, 1-oxo-2-(2,6-dioxopiperidin-3-yl)-4-aminoisoindoline, 1-oxo-2-(2,6-dioxopiperidin-3-yl)-6-aminoisoindoline, 1-oxo-2-(2,6-dioxopiperidin-3-yl)-7-aminoisoindoline, and 1,3-dioxo-2-(2,6-dioxopiperidin-3-yl)-4-aminoisoindoline, respectively, upon hydrogenation.

Example 2

1,3-Dioxo-2-(2,6-dioxopiperidin-3-yl)-5-nitroisoindoline

A mixture of 4-nitrophthalic anhydride (1.7 g, 8.5 mmol), α-aminoglutarimide hydrochloride (1.4 g, 8.5 mmol) and sodium acetate (0.7 g, 8.6 mmol) in glacial acetic acid (30 mL) was heated under reflux for 17 hours. The mixture was concentrated in vacuo and the residue was stirred with methylene chloride (40 mL) and water (30 mL). The aqueous layer was separated, extracted with methylene chloride (2×40 mL). The combined methylene chloride solutions were dried over magnesium sulfate and concentrated in vacuo to give 1.4 g (54%) of 1,3-dioxo-2-(2,6-dioxopiperidin-3-yl)-5-nitroisoindoline as a light brown solid. An analytical sample was obtained by recrystallization from methanol: mp 228.5-229.5° C.; $^1$H NMR (DMSO-$d_6$) δ 11.18 (s, 1H), 8.69-8.65 (d,d J=1.9 and 8.0 Hz, 1H), 8.56 (d, J=1.9 Hz, 1H), 8.21 (d, H=8.2 Hz, 1H), 5.28 (d,d J=5.3 and 12.8 Hz, 1H), 2.93-2.07 (m, 4H); $^{13}$C NMR (DMSO-$d_6$) δ 172.66, 169.47, 165.50, 165.23, 151.69, 135.70, 132.50, 130.05, 124.97, 118.34, 49.46, 30.85, 21.79; Anal. Calcd for $C_{13}H_9N_3O_6$: C, 51.49; H, 2.99; N, 13.86. Found: C, 51.59; H, 3.07; N, 13.73.

1-Oxo-2-(2,6-dioxopiperidin-3-yl)-5-nitroisoindoline, 1-oxo-2-(2,6-dioxopiperidin-3-yl)-4-nitroisoindoline, 1-oxo-2-(2,6-dioxopiperidin-3-yl)-6-nitroisoindoline, and 1-oxo-2-(2,6-dioxopiperidin-3-yl)-7-nitroisoindoline can be obtained by allowing 2,6-dioxopiperidin-3-ammonium chloride to react with methyl 2-bromomethyl-5-nitrobenzoate, methyl 2-bromomethyl-4-nitrobenzoate, methyl 2-bromomethyl-6-nitrobenzoate, and methyl 2-bromomethyl-7-nitrobenzoate, respectively, in dimethylformamide in the presence of triethylamine. The methyl 2-(bromomethyl)nitrobenzoates in turn are obtained from the corresponding methyl esters of nitro-ortho-toluic acids by conventional bromination with N-bromosuccinimide under the influence of light.

Example 3

1-Oxo-2-(2,6-dioxopiperidin-3-yl)-4,5,6,7-tetrafluoroisoindoline

A mixture of 16.25 g of 2,6-dioxopiperidin-3-ammonium chloride, and 30.1 g of methyl 2-bromomethyl-3,4,5,6-tetrafluorobenzoate, and 12.5 g of triethylamine in 100 mL of dimethylformamide is stirred at room temperature for 15 hours. The mixture is then concentrated in vacuo and the residue mixed with methylene chloride and water. The aqueous layer is separated and back-extracted with methylene chloride. The combined methylene chloride solutions are dried over magnesium sulfate and concentrated in vacuo to give 1-oxo-2-(2,6-dioxopiperidin-3-yl)-4,5,6,7-tetrafluoroisoindoline.

In a similar fashion 1-oxo-2-(2,6-dioxopiperidin-3-yl)-4,5,6,7-tetrachloroisoindoline, 1-oxo-2-(2,6-dioxopiperidin-3-yl)-4,5,6,7-tetramethylisoindoline, and 1-oxo-2-(2,6-dioxopiperidin-3-yl)-4,5,6,7-tetramethoxyisoindoline are obtained by substituting equivalent amounts of 2-bromomethyl-3,4,5,6-tetrachlorobenzoate, 2-bromomethyl-3,4,5,6-tetramethylbenzoate, and 2-bromomethyl-3,4,5,6-tetramethoxy benzoate, respectively, for 2-bromomethyl-3,4,5,6-tetrafluorobenzoate.

Example 4

N-Benzyloxycarbonyl-α-methyl-glutamic Acid

To a stirred solution of α-methyl-D,L-glutamic acid (10 g, 62 mmol) in 2 N sodium hydroxide (62 mL) at 0-5° C. was added benzyl chloroformate (12.7 g, 74.4 mmol) over 30 min. After the addition was complete the reaction mixture was stirred at room temperature for 3 hours. During this time the pH was maintained at 11 by addition of 2N sodium hydroxide (33 mL). The reaction mixture was then extracted with ether (60 mL). The aqueous layer was cooled in an ice bath and then acidified with 4N hydrochloric acid (34 mL) to pH=1. The resulting mixture was extracted with ethyl acetate (3×100 mL). The combined ethyl acetate extracts were washed with brine (60 mL) and dried ($MgSO_4$). The solvent was removed in vacuo to give 15.2 g (83%) of N-benzyloxycarbonyl-α-methylglutamic acid as an oil: $^1$H NMR ($CDCl_3$) δ 8.73 (m, 5H), 5.77 (b, 1H), 5.09 (s, 2H), 2.45-2.27 (m, 4H), 2.0 (s, 3H).

In a similar fashion from α-ethyl-D,L-glutamic acid and α-propyl-D,L-glutamic acid, there is obtained N-benzyloxycarbonyl-α-ethylglutamic acid and N-benzyloxycarbonyl-α-propylglutamic acid, respectively.

Example 5

N-Benzyloxycarbonyl-α-methyl-glutamic Anhydride

A stirred mixture of N-benzyloxycarbonyl-α-methylglutamic acid (15 g, 51 mmol) and acetic anhydride (65 mL) was heated at reflux under nitrogen for 30 min. The reaction mixture was cooled to room temperature and then concentrated in vacuo to afford N-benzylcarbonyl-α-methylglutamic anhydride as an oil (15.7 g) which can be used in next reaction without further purification: $^1$H NMR ($CDCl_3$) δ 7.44-7.26 (m, 5H), 5.32-5.30 (m, 2H), 5.11 (s, 1H), 2.69-2.61 (m, 2H), 2.40-2.30 (m, 2H), 1.68 (s, 3H).

In a similar fashion from N-benzyloxycarbonyl-α-ethylglutamic acid and N-benzyloxycarbonyl-α-propylglutamic acid, there is obtained N-benzylcarbonyl-α-ethylglutamic anhydride and N-benzylcarbonyl-α-propylglutamic anhydride, respectively.

Example 6

N-Benzyloxycarbonyl-α-methylisoglutamine

A stirred solution of N-benzylcarbonyl-α-methylglutamic anhydride (14.2 g, 51.5 mmol) in methylene chloride (100 mL) was cooled in an ice bath. Gaseous ammonia was bubbled into the cooled solution for 2 hours. The reaction mixture was stirred at room temperature for 17 hours and then extracted with water (2×50 mL). The combined aqueous extracts were cooled in an ice bath and acidified with 4N hydro-choleric acid (32 mL) to pH 1. The resulting mixture was extracted with ethyl acetate (3×80 mL). The combined ethyl acetate extracts were washed with brine (60 mL), and then dried ($MgSO_4$). The solvent was removed in vacuo to give 11.5 g of N-benzyloxycarbonyl-α-amino-α-methylisoglutamine: $^1$H NMR ($CDCl_3$/DMSO) δ 7.35 (m, 5H), 7.01 (s, 1H), 6.87 (s, 1H), 6.29 (s, 1H), 5.04 (s, 2H), 2.24-1.88 (m, 4H), 1.53 (s, 3H).

In a similar fashion from N-benzylcarbonyl-α-ethylglutamic anhydride and N-benzylcarbonyl-α-propylglutamic anhydride there is obtained N-benzyloxycarbonyl-α-amino-α-ethylisoglutamine and N-benzyloxycarbonyl-α-amino-α-propylisoglutamine, respectively.

Example 7

N-Benzyloxycarbonyl-α-amino-α-methylglutarimide

A stirred mixture of N-benzyloxycarbonyl-α-methylisoglutamine (4.60 g, 15.6 mmol), 1,1'-carbonyldiimidazole (2.80 g, 17.1 mmol), and 4-dimethylaminopyridine (0.05 g) in tetrahydrofuran (50 mL) was heated to reflux under nitrogen for 17 hours. The reaction mixture was then concentrated in vacuo to an oil. The oil was slurried in water (50 mL) for 1 hour. The resulting suspension was filtered and the solid washed with water and air dried to afford 3.8 g of the crude product as a white solid. The crude product was purified by flash chromatography (methylene chloride:ethyl acetate 8:2) to afford 2.3 g (50%) of N-benzyloxycarbonyl-α-amino-α-methylglutarimide as a white solid: mp 150.5-152.5° C.; $^1$H NMR ($CDCl_3$) δ 8.21 (s, 1H), 7.34 (s, 5H), 5.59 (s, 1H), 5.08 (s, 2H), 2.74-2.57 (m, 3H), 2.28-2.25 (m, 1H), 1.54 (s, 3H); $^{13}$C NMR ($CDCl_3$) δ 174.06, 171.56, 154.68, 135.88, 128.06, 127.69, 127.65, 66.15, 54.79, 29.14, 28.70, 21.98; HPLC: Waters Nova-Pak C18 column, 4 micron, 3.9×150 mm, 1 mL/min, 240 nm, 20/80 $CH_3CN/0.1\%$ $H_3PO_4$(aq), 7.56 min (100%); Anal. Calcd For $C_{14}H_{16}N_2O_4$; C, 60.86; H, 5.84; N, 10.14. Found: C, 60.88; H, 5.72; N, 10.07.

In a similar fashion from N-benzyloxycarbonyl-α-amino-α-ethylisoglutamine and N-benzyloxycarbonyl-α-amino-α-propylisoglutamine there is obtained N-benzyloxycarbonyl-α-amino-α-ethylglutarimide and N-benzyloxycarbonyl-α-amino-α-propylglutarimide, respectively.

Example 8

α-Amino-α-methylglutarimide Hydrochloride

N-Benzyloxycarbonyl-α-amino-α-methylglutarimide (2.3 g, 8.3 mmol) was dissolved in ethanol (200 mL) with gentle heat and the resulting solution allowed to cool to room temperature. To this solution was added 4N hydrochloric acid (3 mL) followed by 10% Pd/C (0.4 g). The mixture was hydrogenated in a Parr apparatus under 50 psi of hydrogen for 3 hours. To the mixture was added water (50 mL) to dissolve the product. This mixture was filtered through a Celite pad which was washed with water (50 mL). The filtrate was concentrated in vacuo to afford a solid residue. The solid was slurried in ethanol (20 mL) for 30 min. The slurry was filtered to afford 1.38 g (93%) of α-amino-α-methylglutarimide hydrochloride as a white solid: $^1$H NMR (DMSO-$d_6$) δ 11.25 (s, 1H), 8.92 (s, 2.84-2.51 (m, 2H), 2.35-2.09 (m, 2H), 1.53 (s, 3H); HPLC, Waters Nova-Pak $C_{is}$ column, 4 micron, 1 mL/min, 240 nm, 20/80 $CH_3CN/0.1\%$ $H_3PO_4$(aq), 1.03 min (94.6%).

In a similar fashion from N-benzyloxycarbonyl-α-amino-α-ethylglutarimide and N-benzyloxycarbonyl-α-amino-α-propylglutarimide there is obtained α-amino-α-ethylglutarimide hydrochloride and α-amino-α-propylglutarimide hydrochloride, respectively.

Example 9

3-(3-Nitrophthalimido)-3-methylpiperidine-2,6-dione

A stirred mixture of α-amino-α-methylglutarimide hydrochloride (1.2 g, 6.7 mmol), 3-nitrophthalic anhydride (1.3 g, 6.7 mmol), and sodium acetate (0.6 g, 7.4 mmol) in acetic acid (30 mL) was heated to reflux under nitrogen for 6 hours. The mixture then was cooled and concentrated in vacuo. The resulting solid was slurried in water (30 mL) and methylene chloride (30 mL) for 30 min. The suspension was filtered, the solid was washed with methylene chloride, and dried in vacuo (60° C., <1 mm) to afford 1.44 g (68%) of 3-(3-nitrophthalimido)-3-methylpiperidine-2,6-dione as a off-white solid: mp 265-266.5° C.; $^1$H NMR (DMSO-$d_6$) δ 11.05 (s, 1H), 8.31 (dd, J=1.1 and 7.9 Hz, 1H), 8.16-8.03 (m, 2H), 2.67-2.49 (m, 3H), 2.08-2.02 (m, 1H), 1.88 (s, 3H); $^{13}$C NMR (DMSO-$d_6$) δ 172.20, 171.71, 165.89, 163.30, 144.19, 136.43, 133.04, 128.49, 126.77, 122.25, 59.22, 28.87, 28.49, 21.04; HPLC, Water Nova-Pak/$C_{18}$ column, 4 micron, 1 mL/min, 240 nm, 20/80 $CH_3CN$/0.1% $H_3PO_4$(aq), 7.38 min (98%). Anal. Calcd For $C_{14}H_{11}N_3O_6$: C, 53.00; H, 3.49; N, 13.24. Found: C, 52.77; H, 3.29; N, 13.00.

In a similar fashion from α-amino-α-ethylglutarimide hydrochloride and α-amino-α-propylglutarimide hydrochloride there is obtained 3-(3-nitrophthalimido)-3-ethylpiperidine-2,6-dione and 3-(3-nitrophthalimido)-3-propylpiperidine-2,6-dione, respectively.

Example 10

3-(3-Aminophthalimido)-3-methylpiperidine-2,6-dione 3-(3-Nitrophthalimido)-3-methylpiperidine-2,6-dione (0.5 g, 1.57 mmol) was dissolved in acetone (250 mL) with gentle heat and then cooled to room temperature. To this solution was added 10% Pd/C (0.1 g) under nitrogen. The mixture was hydrogenated in a Parr apparatus at 50 psi of hydrogen for 4 hours. The mixture then was filtered through Celite and the pad washed with acetone (50 mL). The filtrate was concentrated in vacuo to yield a yellow solid. The solid was slurried in ethyl acetate (10 mL) for 30 minutes. The slurry then was filtered and dried (60° C., <1 mm) to afford 0.37 g (82%) of 3-(3-aminophthalimido)-3-methylpiperidine-2,6-dione as a yellow solid: mp 268-269° C.; $^1$H NMR (DMSO-$d_6$) δ 10.98 (s, 1H), 7.44 (dd, J=7.1 and 7.3 Hz, 1H), 6.99 (d, J=8.4 Hz, 1H), 6.94 (d, J=6.9 Hz, 1H), 6.52 (s, 2H), 2.71-2.47 (m, 3H), 2.08-1.99 (m, 1H), 1.87 (s, 3H); $^1$H NMR (DMSO-$d_6$) δ 172.48, 172.18, 169.51, 168.06, 146.55, 135.38, 131.80, 121.51, 110.56, 108.30, 58.29, 29.25, 28.63, 21.00; HPLC, Water Nova-Pak/$C_{is}$ column, 4 micron, 1 mL/min, 240 nm, 20/80 $CH_3CN$/0.1% $H_3PO_4$(aq), 5.62 min (99.18%). Anal. Calcd For $C_{14}H_{13}N_3O_4$: C, 58.53; H, 4.56; N, 14.63. Found: C, 58.60; H, 4.41; N, 14.36.

In a similar fashion from 3-(3-nitrophthalimido)-3-ethylpiperidine-2,6-dione and 3-(3-nitrophthalimido)-3-propylpiperidine-2,6-dione there is obtained 3-(3-aminophthalimido)-3-ethylpiperidine-2,6-dione and 3-(3-aminophthalimido)-3-propylpiperidine-2,6-dione, respectively.

Example 11

Methyl 2-bromomethyl-3-nitrobenzoate

A stirred mixture of methyl 2-methyl-3-nitrobenzoate (17.6 g, 87.1 mmol) and N-bromosuccinimide (18.9 g, 105 mmol) in carbon tetrachloride (243 mL) was heated under gentle reflux with a 100 W light bulb situated 2 cm away shining on the reaction mixture overnight. After 18 hours, the reaction mixture was cooled to room temperature and filtered. The filtrate was washed with water (2×120 mL), brine (120 mL), and dried (MgSO$_4$). The solvent was removed in vacuo to give a yellow solid. The product was purified by flash chromatography (hexane:ethyl acetate 8:2) to give 22 g (93%) of methyl 2-bromomethyl-3-nitrobenzoate as a yellow solid: mp 69-72° C.; $^1$H NMR (CDCl$_3$) δ 8.13-8.09 (dd, J=1.36 and 7.86 Hz, 1H), 7.98-7.93 (dd, J=1.32 and 8.13 Hz, 1H), 7.57-7.51 (t, J=7.97 Hz, 1H), 5.16 (s, 2H), 4.0 (s, 3H); $^1$H NMR (CDCl$_3$) δ 65.84, 150.56, 134.68, 132.64, 132.36, 129.09, 53.05, 22.70; HPLC: Waters Nova-Pak $C_{18}$ column, 4 micron, 1 mL/min, 240 nm, 40/60 $CH_3CN$/0.1% $H_3PO_4$(aq), 8.2 min 99%. Anal. Calcd for $C_9H_8NO_4Br$: C, 39.44; H, 2.94; N, 5.11; Br, 29.15. Found: C, 39.51; H, 2.79; N, 5.02; Br, 29.32.

Example 12

3-(1-Oxo-4-nitroisoindolin-1-yl)-3-methylpiperidine-2,6-done

To a stirred mixture of α-amino-α-methylglutarimide hydrochloride (2.5 g, 14.0 mmol) and methyl 2-bromomethyl-3-nitrobenzoate (3.87 g, 14.0 mmol in dimethylformamide (40 mL) was added triethylamine (3.14 g, 30.8 mmol). The resulting mixture was heated to reflux under nitrogen for 6 horns. The mixture was cooled and then concentrated in vacuo. The resulting solid was slurried in water (50 mL) and $CH_2Cl_2$ for 30 min. The slurry was filtered, the solid washed with methylene chloride, and dried in vacuo (60° C., <1 mm) to afford 2.68 g (63%) of 3-(1-oxo-4-nitroisoindolin-1-yl)-3-methylpiperidine-2,6-dione as a off-white solid: mp 233-235° C.; $^1$H NMR (DMSO-$d_6$) δ 10.95 (s, 1H), 8.49-8.46 (d, J=8.15 Hz, 1H), 8.13-8.09 (d, J=7.43 Hz, 1H), 7.86-7.79 (t, J=7.83 Hz, 1H), 5.22-5.0 (dd, J=49.35 and 34.6 Hz, 2H), 2.77-2.49 (m, 3H), 2.0-1.94 (m, 1H), 1.74 (S, 3H); $^{13}$C NMR (DMSO-$d_6$) δ 173.07, 172.27, 164.95, 143.15, 137.36, 135.19, 130.11, 129.32, 126.93, 57.57, 48.69, 28.9, 27.66, 20.6; HPLC, Waters Nova-Pak $C_{18}$ column, 4 micron, 1 mL/min. 240 nm, 20/80 $CH_2CN$/0.1% $H_3PO_4$(aq), 4.54 min 99.6%. Anal. Calcd for $C_{14}H_{13}N_3O_5$: C, 55.45; H, 4.32; N, 13.86. Found: C, 52.16; H, 4.59; N, 12.47.

By substituting equivalent amounts of α-amino-α-ethylglutarimide hydrochloride and α-amino-α-propylglutarimide hydrochloride for α-amino-α-methylglutarimide hydrochloride, there is obtained respectively 3-(1-oxo-4-nitroisoindolin-1-yl)-3-ethylpiperidine-2,6-dione and 3-(1-oxo-4-nitroisoindolin-1-yl)-3-propylpiperidine-2,6-dione.

Example 13

3-(1-Oxo-4-aminoisoindolin-1-yl)-3-methylpiperidine-2,6-dione 3-(1-Oxo-4-nitroisoindolin-1-yl)-3-methylpiperidine-2,6-dione (1.0 g, 3.3 mmol) was dissolved in methanol (500 mL) with gentle heat and allowed to cool to room temperature. To this solution was added 10% Pd/C (0.3 g) under nitrogen. The mixture was hydrogenated in a Parr apparatus at 50 psi of hydrogen for 4 hours. The mixture was filtered through Celite and the Celite washed with methanol (50 mL). The filtrate was concentrated in vacuo to an off white solid. The solid was slurried in methylene chloride (20 mL) for 30 min. The slurry was then filtered and the solid dried (60° C., <1 nm) to afford 0.54 g (60%) of 3-(1-oxo-4-aminoisoindolin-1-yl)-3-methylpiperidine-2,6-dione as a white solid: mp 268-270° C.; $^1$H NMR (DMSO-$d_6$) δ 10.85 (s, 1H), 7.19-7.13 (t, J=7.63 Hz, 1H), 6.83-6.76 (m, 2H), 5.44 (s, 2H), 4.41 (s, 2H), 2.71-2.49 (m, 3H), 1.9-1.8 (m, 1H), 1.67 (s, 3H); $^{13}$C NMR (DMSO-$d_6$)

δ 173.7, 172.49, 168.0, 143.5, 132.88, 128.78, 125.62, 116.12, 109.92, 56.98, 46.22, 29.04, 27.77, 20.82; HPLC, Waters Nova-Pak/C18 column, 4 micron, 1 mL/min, 240 nm, 20/80 $CH_3CN/0.1\%$ $H_3PO_4$(aq), 1.5 min (99.6%); Anal. Calcd for $C_{14}H_{15}N_3O_3$: C, 61.53; 1-1; N, 15.38. Found: C, 58.99; 14, 5.48; N, 14.29.

From 3-(1-oxo-4-nitroisoindolin-1-yl)-3-ethylpiperidine-2,6-dione and 3-(1-oxo-4-nitroisoindolin-1-yl)-3-propylpiperidine-2,6-dione there is similarly obtained 3-(1-oxo-4-aminoisoindolin-1-yl)-3-ethylpiperidine-2,6-dione and 3-(1-oxo-4-aminoisoindolin-1-yl)-3-propylpiperidine-2,6-dione, respectively.

Example 14

S-4-Amino-2-(2,6-dioxopiperidin-3-yl)isoindoline-1,3-dione

A. 4-Nitro-N-ethoxycarbonylphthalimide

Ethyl chloroformate (1.89 g, 19.7 mmol) was added dropwise over 10 min to a stirred solution of 3-nitrophthalimide (3.0 g, 15.6 mmol) and triethylamine (1.78 g, 17.6 mmol) in dimethylformamide (20 mL) at 0-5° C. under nitrogen. The reaction mixture was allowed to warm to room temperature and stirred for 4 hours. The mixture was then slowly added to an agitated mixture of ice and water (60 mL). The resulting slurry was filtered and the solid was crystallized from chloroform (15 mL) and pet ether (15 mL) to afford 3.1 g (75%) of the product as an off-white solid: mp 100-100.5° C.; $^1H$ NMR ($CDCl_3$) δ 8.25 (d, J=7.5 Hz, 1H), 8.20 (d, J=8.0 Hz, 1H), 8.03 (t, J=7.9 Hz, 1H), 4.49 (q, J=7.1 Hz, 2H), 1.44 (t, J=7.2 Hz, 3H); $^{13}C$ NMR ($CDCl_3$) δ 161.45, 158.40, 147.52, 145.65, 136.60, 132.93, 129.65, 128.01, 122.54, 64.64, 13.92; HPLC, Waters Nova-Pak/C18, 3.9×150 mm, 4 micron, 1 mL/min, 240 nm, 30/70 $CH_3CN/0.1\%$ $H_3PO_4$(aq), 5.17 min (98.11%); Anal. Calcd for $C_{11}H_8N_2O_6$: C, 50.00; H, 3.05; N, 10.60. Found: C, 50.13; H, 2.96; N, 10.54.

B. L-Butyl N-(4-nitrophthaloyl)-L-glutamine

A stirred mixture of 4-nitro-N-ethoxycarbonylphthalimide (1.0 g, 3.8 mmol), L-glutamine t-butyl ester hydrochloride (0.90 g, 3.8 mmol) and triethylamine (0.54 g, 5.3 mmol) in tetrahydrofuran (30 mL) was heated to reflux for 24 hours. The tetrahydrofuran was removed in vacuo and the residue was dissolved in methylene chloride (50 mL). The methylene chloride solution was washed with water (2×15 mL), brine (15 mL) and then dried (sodium sulfate). The solvent was removed in vacuo and the residue was purified by flash chromatograph (7:3 methylene chloride:ethyl acetate) to give 0.9 g (63%) of a glassy material: $^1H$ NMR ($CDCl_3$) δ8.15 (d, J=7.9 Hz, 2H), 7.94 (t, J=7.8 Hz, 1H), 5.57 (b, 2H), 4.84 (dd, J=5.1 and 9.7 Hz, 1H), 2.53-2.30 (m, 4H), 1.43 (s, 9H); HPLC, Wasters Nova-Pak/C18, 3.9×150 mm, 4 micron, 1 mL/min, 240 nm, 30/70 $CH_3CN/0.1\%$ $H_3PO_4$(aq), 6.48 min (99.68%); Chiral Analysis, Daicel Chiral Pak AD, 0.4×25 Cm, 1 mL/min, 240 nm, 5.32 min (99.39%); Anal. Calcd for $C_{17}H_{19}N_3O_7$: C, 54.11; H, 5.08; N, 11.14. Found: C, 54.21; H, 5.08; N, 10.85.

C. N-(4-Nitrophthaloyl)-L-glutamine

Hydrogen chloride gas was bubbled into a stirred 5° C. solution of t-butyl N-(4-nitrophthaloyl)-L-glutamine (5.7 g, 15.1 mmol) in methylene chloride (100 mL) for 25 min. The mixture was then stirred at room temperature for 16 hours. Ether (50 mL) was added and the resulting mixture was stirred for 30 min. The resulting slurry was filtered to yield 4.5 g of crude product as a solid, which was used directly in the next reaction: $^1H$ NMR (DMSO-$d_6$) δ 8.36 (dd, J=0.8 and 8.0 Hz, 1H), 8.24 (dd, J=0.8 and 7.5 Hz, 1H), 8.11 (1, J=7.9 Hz, 1H), 7.19 (b, 1H), 6.72 (b, 1H), 4.80 (dd, J=3.5 and 8.8 Hz, 1H), 2.30-2.10 (m, 4H).

D. (S)-2-(2,6-dioxo(3-piperidyl)-4-nitroisoindoline-1,3-dione

A stirred suspension of N-(4-nitrophthaloyl)-L-glutamine (4.3 g, 13.4 mmol) in anhydrous methylene chloride (170 mL) was cooled to −40° C. (IPA/dry ice bath). Thionyl chloride (1.03 mL, 14.5 mmol) was added dropwise to the mixture followed by pyridine (1.17 mL, 14.5 mmol). After 30 minutes, triethylamine (2.06 mL, 14.8 mmol) was added and the mixture was stirred at −30 to −40° C. for 3 hours. The mixture was allowed to warm to room temperature, filtered and washed with methylene chloride to afford 2.3 g (57%) of the crude product. Recrystallization from acetone (300 mL) afforded 2 g of the product as a white solid: mp 259.0-284.0° C. (dec.); $^1H$ NMR (DMSO-$d_6$) δ 11.19 (s, 1H), 8.34 (d, J=7.8 Hz, 1H), 8.23 (d, J=7.1 Hz, 1H), 8.12 (t, J=7.8 Hz, 1H), 5.25-5.17 (dd, J=5.2 and 12.7 Hz, 1H), 2.97-2.82 (m, 1H), 2.64-2.44 (m, 2H), 2.08-2.05 (m, 1H); $^{13}C$ NMR (DMSO-$d_6$) δ 172.67, 169.46, 165.15, 162.50, 144.42, 136.78, 132.99, 128.84, 127.27, 122.53, 49.41, 30.84, 21.71; HPLC, Waters Nova-Pak/C18, 3.9×150 mm, 4 micron, 1 mL/min, 240 nm, 10/90 $CH_3CN/0.1\%$ $H_3PO_4$(aq) 4.27 min (99.63%); Anal. Calcd for $C_{13}H_9N_3O_6$: C, 51.49; H, 2.99; N, 13.86. Found: C, 51.67; H, 2.93; N, 13.57.

E. S-4-Amino-2-(2,6-dioxopiperidin-3-yl)isoindoline-1,3-dione

A mixture of (S)-3-(4'-nitrophthalimido)-piperidine-2,6-dione (0.76 g, 2.5 mmol) and 10% Pd/C (0.3 g) in acetone (200 mL) was hydrogenated in a Parr-Shaker apparatus at 50 psi of hydrogen for 24 hours. The mixture was filtered through celite and the filtrate was concentrated in vacuo. The solid residue was slurried in hot ethyl acetate for 30 min and filtered to yield 0.47 g (69%) of the product as a yellow solid: mp 309-310° C.; $^1H$ NMR (DMSO-$d_6$) δ 11.10 (s, 1H), 7.47 (dd, J=7.2 and 8.3 Hz, 1H), 7.04-6.99 (dd, J=6.9 and 8.3 Hz, 2H), 6.53 (s, 2H), 5.09-5.02 (dd, J=5.3 and 12.4 Hz, 1H), 2.96-2.82 (m, 1H), 2.62-2.46 (m, 2H), 2.09-1.99 (m, 1H); $^{13}C$ NMR (DMSO-$d_6$) δ 172.80, 170.10, 168.57, 167.36, 146.71, 135.44, 131.98, 121.69, 110.98, 108.54, 48.48, 30.97, 22.15; HPLC, Waters Nova-Pak/C18, 3.9×150 mm, 4 micron, 1 mL/min, 240 nm, 15/85 $CH_3CN/0.1\%$ $H_3PO_4$(aq) 4.99 min (98.77%); Chiral analysis, Daicel Chiral Pak AD, 0.46×25 cm, 1 mL/min, 240 nm, 30/70 Hexane/IPA 9.55 min (1.32%), 12.55 min (97.66%); Anal. Calcd for $C_{13}H_{11}N_3O_4$: C, 57.14; H, 4.06; N, 15.38. Found: C, 57.15; H, 4.15; N, 14.99.

Example 15

R-4-Amino-2-(2,6-dioxopiperidin-3-yl))isoindoline-1,3-dione

A. t-Butyl N-(4-nitrophthaloyl)-D-glutamine

A stirred mixture of 4-nitro-N-ethoxycarbonyl-phthalimide (5.9 g, 22.3 mmol), D-glutamine t-butyl ester (4.5 g, 22.3 mmol) and triethylamine (0.9 g, 8.9 mmol) in tetrahydrofuran (100 mL) was refluxed for 24 hours. The mixture was diluted with methylene chloride (100 mL) and washed with water (2×50 mL), brine (50 mL) and then dried. The solvent was removed in vacuo and the residue was purified by flash chromatography (2% $CH_3OH$ in methylene chloride) to afford 6.26 g (75%) of the product as a glassy material: $^1H$ NMR ($CDCl_3$) δ 8.12 (d, J=7.5 Hz, 2H), 7.94 (dd, J=7.9 and 9.1 Hz, 1H), 5.50 (b, 1H), 5.41 (b, 1H), 4.85 (dd, J=5.1 and 9.8 Hz, 1H), 2.61-2.50 (m, 2H), 2.35-2.27 (m, 2H), 1.44 (s, 9H); $^{13}C$ NMR ($CDCl_3$) δ 173.77, 167.06, 165.25, 162.51, 145.07, 135.56, 133.78, 128.72, 127.27, 123.45, 83.23, 53.18, 32.27, 27.79, 24.42; HPLC, Waters Nova-Pak/C18, 3.9×150 mm, 4 micron, 1 mL/min, 240 nm, 25/75 $CH_3CN$/0.1% $H_3PO_4$(aq) 4.32 min (99.74%); Chiral analysis, Daicel Chiral Pak AD, 0.46×25 cm, 1 mL/min, 240 nm, 55/45 Hexane/IPA 5.88 min (99.68%); Anal. Calcd for $C_{17}H_{19}N_3O_7$: C, 54.11; H, 5.08; N, 11.14. Found: C, 54.25; H, 5.12; N, 10.85.

B. N-(4-Nitrophthaloyl)-D-glutamine

Hydrogen chloride gas was bubbled into a stirred 5° C. solution of t-butyl N-(4-nitrophthaloyl)-D-glutamine (5.9 g, 15.6 mmol) in methylene chloride (100 mL) for 1 hour then stirred at room temperature for another hour. Ether (100 mL) was added and stirred for another 30 minutes. The mixture was filtered, the solid was washed with ether (60 mL) and dried (40° C., <1 mm Hg) to afford 4.7 g (94%) of the product: $^1H$ NMR (DMSO-$d_6$) δ 8.33 (d, J=7.8 Hz, 1H), 8.22 (d, J=7.2 Hz, 1H), 8.11 (t, J=7.8 Hz, 1H), 7.19 (b, 1H), 6.72 (1, 1H), 4.81 (dd, J=4.6 and 9.7 Hz, 1H), 2.39-2.12 (m, 4H); $^{13}C$ NMR (DMSO-$d_6$) δ 173.21, 169.99, 165.41, 162.73, 144.45, 136.68, 132.98, 128.80, 127.23, 122.52, 51.87, 31.31, 23.87.

C(R)-2-(2,6-dioxo(3-piperidyl)-4-nitroisoindoline-1,3-dione

A stirred suspension of N-(4'-nitrophthaloyl)-D-glutamine (4.3 g, 13.4 mmol) in anhydrous methylene chloride (170 mL) was cooled to −40° C. with isopropanol/dry ice bath. Thionyl chloride (1.7 g, 14.5 mmol) was added dropwise followed by pyridine (1.2 g, 14.5 mmol). After 30 min, triethylamine (1.5 g, 14.8 mmol) was added and the mixture was stirred at −30 to −40° C. for 3 hours. The mixture was filtered, the solid washed with methylene chloride (50 mL) and dried (60° C., <1 mm Hg) to give 2.93 g of the product. Another 0.6 g of the product was obtained from the methylene chloride filtrate. Both fractions were combined (3.53 g) and recrystallized from acetone (450 mL) to afford 2.89 g (71%) of the product as a white solid: mp 256.5-257.5° C.; $^1H$ NMR (DMSO-$d_6$) δ 11.18 (s, 1H), 8.34 (dd, 0.8 and 7.9 Hz, 1H), 8.23 (dd, J=0.8 and 7.5 Hz, 1H), 8.12 (t, J=7.8 Hz, 1H), 5.22 (dd, J=5.3 and 12.8 Hz, 1H), 2.97-2.82 (m, 1H), 2.64-2.47 (m, 2H), 2.13-2.04 (m, 1H); $^{13}C$ NMR (DMSO-$d_6$) δ 172.66, 169.44, 165.14, 162.48, 144.41, 136.76, 132.98, 128.83, 127.25, 122.52, 49.41, 30.83, 21.70; HPLC, Waters Nova-Pak/CIS, 3.9×150 mm, 4 micron, 1 mL/min, 240 nm, 10/90 $CH_3CN$/0.1% $H_3PO_4$(aq) 3.35 min (100%); Anal. Calcd for $C_{13}H_9N_3O_6$: C, 51.49; H, 2.99; N, 13.86. Found: C, 51.55; H, 2.82; N, 13.48.

D. (R)-4-Amino-2-(2,6-dioxopiperidin-3-yl)isoindoline-1,3-dione

A mixture of R-3-(4'-nitrophthalimido)-piperidine-2,6-dione (1.0 g, 3.3 mmol) and 10% Pd/C (0.2 g) in acetone (250 mL) was hydrogenated in a Parr-Shaker apparatus at 50 psi of hydrogen for 4 hours. The mixture was filtered through celite and the fitrate was concentrated in vacuo. The resulting yellow solid was slurried in hot ethyl acetate (20 mL) for 30 min to give after filtration and drying 0.53 g (59%) of the product as a yellow solid: mp 307.5-309.5° C.; $^1H$ NMR (DMSO-$d_6$) δ 11.06 (s, 1H), 7.47 (dd, J=7.0 and 8.4 Hz, 1H), 7.02 (dd, J=4.6 and 8.4 Hz, 2H), 6.53 (s, 2H), 5.07 (dd, J=5.4 and 12.5 Hz, 1H), 2.95-2.84 (m, 1H), 2.62-2.46 (m, 2H), 2.09-1.99 (m, 1H); $^{13}C$ NMR. (DMSO-$d_6$) δ 172.78, 170.08, 168.56, 167.35, 146.70, 135.43, 131.98, 121.68, 110.95, 108.53, 48.47, 30.96, 22.14; HPLC, Waters Nove-Pak/C18, 3.9×150 mm, 4 micron, 1 mL/min, 240 nm, 10/90 $CH_3CN$/0.1% $H_3PO_4$(aq) 3.67 min (99.68%); Chiral analysis, Daicel Chiral Pak AD, 0.46×25 cm, 1 mL/min, 240 nm, 30/70 Hexane/IPA 7.88 min (97.48%); Anal. Calcd for $C_{13}H_{11}N_3O_4$: C, 57.14; H, 4.06; N, 15.38. Found: C, 57.34; H, 3.91; N, 15.14.

Example 16

3-(4-Amino-1-oxoisoindolin-2-yl)piperidine-2,6-dione

A. Methyl 2-bromomethyl-3-nitrobenzoate

A stirred mixture of methyl 2-methyl-3-nitrobenzoate (14.0 g, 71.7 mmol) and N-bromosuccinimide (15.3 g, 86.1 mmol) in carbon tetrachloride (200 mL) was heated under gentle reflux for 15 hours while a 100 W bulb situated 2 cm away was shining on the flask. The mixture was filtered and the solid was washed with methylene chloride (50 mL). The filtrate was washed with water (2×100 mL), brine (100 mL) and dried. The solvent was removed in vacuo and the residue was purified by flash chromatography (hexane/ethyl acetate, 8/2) to afford 19 g (96%) of the product as a yellow solid: mp 70.0-71.5° C.; $^1H$ NMR ($CDCl_3$) δ 8.12-8.09 (dd, J=1.3 and 7.8 Hz, 1H), 7.97-7.94 (dd, J=1.3 and 8.2 Hz, 1H), 7.54 (t, J=8.0 Hz, 1H), 5.15 (s, 2H), 4.00 (s, 3H); $^{13}C$ NMR ($CDCl_3$) δ 165.85, 150.58, 134.68, 132.38, 129.08, 127.80, 53.06, 22.69; HPLC, Water Nove-Pak/C18, 3.9×150 mm, 4 micron, 1 mL/min, 240 nm, 40/60 $CH_3CN$/0.1% $H_3PO_4$(aq) 7.27 min (98.92%); Anal. Calcd for $C_9H_8NO_4Br$: C, 39.44; H, 2.94; N, 5.11; Br, 29.15. Found: C, 39.46; H, 3.00; N, 5.00; Br, 29.11.

B. t-Butyl N-(1-oxo-4-nitroisoindolin-2-yl)-L-glutamine

Triethylamine (2.9 g, 28.6 mmol) was added dropwise to a stirred mixture of methyl 2-bromomethyl-3-nitrobenzoate (3.5 g, 13.0 mmol) and L-glutamine t-butyl ester hydrochloride (3.1 g, 13.0 mmol) in tetrahydrofuran (90 mL). The mixture was heated to reflux for 24 hours. To the cooled mixture was added methylene chloride (150 mL) and the mixture was washed with water (2×40 mL), brine (40 mL) and dried. The solvent was removed in vacuo and the residue was purified by flash chromatography (3% $CH_3OH$ in methylene chloride) to afford 2.84 g (60%) of crude product which was used directly in the next reaction: $^1H$ NMR ($CDCl_3$) δ 8.40 (d, J=8.1 Hz, 1H), 8.15 (d, J=7.5 Hz, 1H), 7.71 (t, J=7.8 Hz, 1H), 5.83 (s, 1H), 5.61 (s, 1H), 5.12 (d, J=19.4 Hz, 1H), 5.04-4.98 (m, 1H), 4.92 (d, J=19.4 Hz, 1H), 2.49-2.22 (m, 4H), 1.46 (s, 9H); HPLC, Waters Nova-Pak/C18, 3.9×150 mm, 4 micron, 1 mL/min, 240 nm, 25/75 $CH_3CN$/0.1% $H_3PO_4$(aq) 6.75 min (99.94%).

C. N-(1-Oxo-4-nitroisoindolin-2-yl)-L-glutamine

Hydrogen chloride gas was bubbled into a stirred 5° C. solution of t-butyl N-(1-oxo-4-nitro-isoindolin-2-yl)-L-glutamine (3.6 g, 9.9 mmol) in methylene chloride (60 mL)

for 1 hour. The mixture was then stirred at room temperature for another hour. Ether (40 mL) was added and the resulting mixture was stirred for 30 minutes. The slurry was filtered, washed with ether and dried to afford 3.3 g of the product: $^1$H NMR (DMSO-$d_6$) δ 8.45 (d, J=8.1 Hz, 1H), 8.15 (d, J=7.5 Hz, 1H), 7.83 (t, J=7.9 Hz, 1H), 7.24 (s, Hi), 6.76 (s, 1H), 4.93 (s, 2H), 4.84-4.78 (dd, J=4.8 and 10.4 Hz, 1H), 2.34-2.10 (m, 4H); $^{13}$C NMR (DMSO-$d_6$) δ 173.03, 171.88, 165.96, 143.35, 137.49, 134.77, 130.10, 129.61, 126.95, 53.65, 48.13, 31.50, 24.69; Anal. Calcd for $C_{13}H_{13}N_3O_6$: C, 50.82; H, 4.26; N, 13.68. Found: C, 50.53; H, 4.37; N, 13.22.

D. (S)-3-(1-Oxo-4-nitroisoindolin-2-yl)piperidine-2,6-dione

A stirred suspension mixture of N-(1-oxo-4-nitroisoindolin-2-yl)-L-glutamine (3.2 g, 10.5 mmol) in anhydrous methylene chloride (150 mL) was cooled to −40° C. with isopropanol/dry ice bath. Thionyl chloride (0.82 mL, 11.3 mmol) was added dropwise to the cooled mixture followed by pyridine (0.9 g, 11.3 mmol). After 30 triethylamine (1.2 g, 11.5 mmol) was added and the mixture was stirred at −30 to −40° C. for 3 hours. The mixture was poured into ice water (200 mL) and the aqueous layer was extracted with methylene chloride (40 mL). The methylene chloride solution was washed with water (2×60 mL), brine (60 mL) and dried. The solvent was removed in vacuo and the solid residue was slurried with ethyl acetate (20 mL) to give 2.2 g (75%) of the product as a white solid: mp 285° C.; $^1$H NMR (DMSO-$d_6$) δ 11.04 (s, 1H), 8.49-8.45 (dd, J=1.8 and 82 Hz, 1H), 8.21-4.17 (dd, J=7.3 Hz, 1H), 7.84 (t, J=7.6 Hz, 1H), 5.23-5.15 (dd, J=4.9 and 13.0 Hz, 1H), 4.96 (dd, J=19.3 and 32.4 Hz, 2H), 3.00-2.85 (m, 1H), 2.64-2.49 (m, 2H), 2.08-1.98 (m, 1H); $^{13}$C NMR (DMSO-$d_6$) δ 172.79, 170.69, 165.93, 143.33, 137.40, 134.68, 130.15, 129.60, 127.02, 51.82, 48.43, 31.16, 22.23; HPLC, Waters Nove-Pak/C18, 3.9×150 mm, 4 micron, 1 mL/min, 240 nm, 20/80 $CH_3CN$/0.1% $H_3PO_4$(aq) 3.67 min (100%); Anal. Calcd for $C_{13}H_{11}N_3O_5$: C, 53.98; H, 3.83; N, 14.53. Found: C, 53.92; H, 3.70; N, 14.10.

E. (S)-3-(1-Oxo-4-aminoisoindolin-2-yl)piperidine-2.6 dione

A mixture of (S)-3-(1-oxo-4-nitroisoindolin-2-yl)piperidine-2,6-dione (1.0 g, 3.5 mmol) and 10% Pd/c (0.3 g) in methanol (600 mL) was hydrogenated in a Parr-Shaker apparatus at 50 psi of hydrogen for 5 hours. The mixture was filtered through Celite and the filtrate was concentrated in vacuo. The solid was slurried in hot ethyl acetate for 30 min, filtered and dried to afford 0.46 g (51%) of the product as a white solid: mp 235.5-239° C.; $^1$H NMR (DMSO-$d_6$) δ 11.01 (s, 1H), 7.19 (t, J=7.6 Hz, 1H), 6.90 (d, J=7.3 Hz, 1H), 6.78 (d, J=7.8 Hz, 1H), 5.42 (s, 2H), 5.12 (dd, J=5.1 and 13.1 Hz, 1H), 4.17 (dd, J=17.0 and 28.8 Hz, 2H), 2.92-2.85 (m, 1H), 2.64-2.49 (m, 1H), 2.34-2.27 (m, 1H), 2.06-1.99 (m, 1H); $^{13}$C NMR (DMSO-$d_6$) δ 172.85, 171.19, 168.84, 143.58, 132.22, 128.79, 125.56, 116.37, 110.39, 51.48, 45.49, 31.20, 22.74; HPLC, Waters Nova-Pak/C18, 3.9×150 mm, 4 micron, 1 mL/min, 240 nm, 10/90 $CH_3CN$/0.1% $H_3PO_4$(aq) 0.96 min (100%); Chiral analysis, Daicel Chiral Pak AD, 40/60 Hexane/IPA, 6.60 min (99.42%); Anal. Calcd for $C_{13}H_{13}N_3O_3$: C, 60.23; H, 5.05; N, 16.21. Found: C, 59.96; H, 4.98; N, 15.84.

Example 17

3-(4-Amino-1-oxoisoindolin-2yl)-3-methylpiperidine-2,6-dione

A. N-Benzyloxycarbonyl-3-amino-3-methylpiperidine-2,6-dione

A stirred mixture of N-benzyloxycarbonyl-α-methyl-isoglutamine (11.3 g, 38.5 mmol), 1,1'-carbonyldiimidazole (6.84 g, 42.2 mmol) and 4-dimethylaminopyridine (0.05 g) in tetrahydrofuran (125 mL) was heated to reflux under nitrogen for 19 hours. The reaction mixture was concentrated in vacuo to an oil. The oil was slurried in water (50 mL) for 1 hour then filtered, washed with water, air dried to afford 7.15 g of white solid. The crude product was purified by flash chromatography (2:8 ethyl acetate:methylene chloride) to afford 6.7 g (63%) of the product as a white solid: mp 151-152° C.; $^1$H NMR (CDCl$_3$) δ 8.24 (s, 1H), 7.35 (s, 5H), 5.6 (s, 1H), 5.09 (s, 2H), 2.82-2.53 (m, 3H), 2.33-2.26 (m, 1H), 1.56 (s, 3H); $^{13}$C NMR (CDCl$_3$) δ 174.4, 172.4, 154.8, 136.9, 128.3, 127.8, 127.7, 65.3, 54.6, 29.2, 29.0, 22.18; HPLC: Waters Nova-Pak/C$_{18}$ column, 4 micron, 3.9×150 mm, 1 ml/min, 240 nm, 20/80 $CH_3CN$/$H_3PO_{4(aq)}$, 6.6 min, 100%). Anal. Calcd for $C_{14}H_{16}N_2O_4$. Theory: C, 60.86; H, 5.84; N, 10.14. Found: C, 60.94; H, 5.76; N, 10.10.

B. 3-Amino-3-methylpiperidine-2,6-dione

N-benzyloxycarbonyl-3-amino-3-methylpiperidine-2,6-dione (3.0 g, 10.9 mmol) was dissolved in ethanol (270 mL) with gentle heat and then cooled to room temperature. To this solution was added 4 N HCl (7 mL) followed by 10% Pd/C (0.52 g). The mixture was hydrogenated under 50 psi of hydrogen for 3 hours. To the mixture was then added water (65 mL) to dissolve the product. The mixture was filtered through a celite pad and the =lite pad washed with water (100 mL). The filtrate was concentrated in vacuo to a solid residue. This solid was slurried in ethanol (50 mL) for 30 min. The slurry was filtered to afford 3.65 g (94%) of the product as a white solid: $^1$H NMR (DMSO-$d_6$) δ 11.25 (s, 1H), 8.9 (s, 3H), 2.87-2.57 (m, 2H), 2.35-2.08 (m, 2H), 1.54 (s, 3H); HPLC (Waters Nova-Pak/C$_{is}$ column, 4 micron, 1 ml/min, 240 nm, 15/85 $CH_3CN$/$H_3PO_{4(aq)}$, 1.07 min, 100%).

C. 3-Methyl-3-(4-nitro-1-oxoisoindolin-2-yl)piperidine-2,6-dione

To a stirred mixture of α-amino-α-methyl-glutarimide hydrochloride (2.5 g, 14.0 mmol) and methyl 2-bromomethyl-3-nitro benzoate (3.87 g, 14 mmol in dimethylformamide (40 mL) was added triethylamine (3.14 g, 30.8 mmol) under nitrogen. The mixture was heated to reflux for 6 hours. The mixture was cooled and then concentrated in vacuo. The solid residue was slurried in water (50 mL) and methylene chloride for 30 min. The slurry was filtered and the solid washed with methylene chloride and dried (60° C., <1 mm). Recrystallization from methanol (80 mL) yielded 0.63 g (15%) of the product as an off white solid: mp 195-197° C.; $^1$H NMR (DMSO-$d_6$) δ 10.95 (s, 1H), 8.49-8.46 (d, J=8.2 Hz, 1H), 8.13-8.09 (d, J=7.4 Hz, 1H), 7.86-7.79 (t, J=7.8 Hz, 1H), 5.22-5.0 (dd, J=19.4 and 34.6 Hz, 2H), 2.77-2.49 (m, 3H), 2.0-1.94 (m, 1H), 1.74 (S, 3H); $^{13}$C NMR (DMSO-$d_6$) δ 173.1, 172.3, 165.0, 143.2, 137.4, 135.2, 130.1, 129.3, 126.9, 57.6, 48.7, 28.9, 27.7, 20.6; HPLC (Waters Nova-Pak/C$_{is}$ column, 4 micron, 1 mL/min. 240 nm, 20/80 $CH_3CN$/H$_3$ PO$_{4(aq)}$, 4.54 min, 99.6%); Anal Calcd. For C$_{14}$H$_{13}$N$_3$O$_5$; C, 55.45; H, 4.32; N, 13.86. Found: C, 55.30; H, 4.48; N, 13.54.

D. 3-Methyl-3-(4-amino-1-oxoisoindolin-2yl)piperidine-2,6-dione

3-Methyl-3-(4-nitro-1-oxoisoindolin-2-yl)piperidine-2,6-dione (1.0 g, 3.3 mmol) was dissolved in methanol (500 mL) with gentle heat and then cooled to room temperature. To this solution was added 10% Pd/C (0.3 g) under nitrogen. The mixture was hydrogenated in a Parr-Shaker apparatus at 50 psi of hydrogen for 4 hours. The mixture was filtered through celite pad and the celite pad washed with methanol (50 mL). The filtrate was concentrated in vacuo to a off white solid. The solid was slurried in methylene chloride (20 mL) for 30 min. The slurry was filtered and the solid dried (60° C., <1 mm). The solid was to recrystallized from methanol (3 times, 100 mL/time) to yield 0.12 g (13.3%) of the product as a white solid: mp 289-292° C.; $^1$H NMR (DMSO-d$_6$) δ 10.85 (s, 1H), 7.19-7.13 (t, J=7.6 Hz, 1H), 6.83-6.76 (m, 2H), 5.44 (s, 2H), 4.41 (s, 2H), 2.71-2.49 (m, 3H), 1.9-1.8 (m, 1H), 1.67 (s, 3H); $^{13}$C NMR (DMSO-d$_6$) δ 173.7, 172.5, 168.0, 143.5, 132.9, 128.8, 125.6, 116.1, 109.9, 57.0, 46.2, 29.0, 27.8, 20.8; HPLC (Waters Nova-Pak/C$_{is}$ column, 4 micron, 1 ml/min, 240 nm, 20/80 CH$_3$CN/H$_3$PO$_{4(aq)}$, 1.5 min, 99.6%); Anal. Calcd. For C$_{14}$H$_{15}$N$_3$O$_3$; C, 61.53; H, 5.53; N, 15.38. Found: C, 61.22; H, 5.63; N, 15.25.

Example 18

Tablets, each containing 50 mg of 1,3-dioxo-2-(2,6-dioxopiperidin-3-yl)-5-aminoisoindoline, can be prepared in the following manner

| Constituents (for 1000 tablets) | |
|---|---|
| 1,3-dioxo-2-(2,6-dioxo-piperidin-3-yl)-5-amino-isoindoline | 50.0 g |
| lactose | 50.7 g |
| wheat starch | 7.5 g |
| polyethylene glycol 6000 | 5.0 g |
| talc | 5.0 g |
| magnesium stearate | 1.8 g |
| demineralized water | q.s. |

The solid ingredients are first forced through a sieve of 0.6 mm mesh width. The active ingredient, lactose, talc, magnesium stearate and half of the starch then are mixed. The other half of the starch is suspended in 40 mL of water and this suspension is added to a boiling solution of the polyethylene glycol in 100 mL of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

Example 19

Tablets, each containing 100 mg of 1,3-dioxo-2-(2,6-dioxopiperidin-3-yl)-5-aminoisoindoline, can be prepared in the following manner:

| Constituents (for 1000 tablets) | |
|---|---|
| 1,3-dioxo-2-(2,6-dioxo-piperidin-3-yl)-5-amino-isoindoline | 100.0 g |
| lactose | 100.0 g |
| wheat starch | 47.0 g |
| magnesium stearate | 3.0 g |

All the solid ingredients are first forced through a sieve of 0.6 mm mesh width. The active ingredient, lactose, magnesium stearate and half of the starch then are mixed. The other half of the starch is suspended in 40 mL of water and this suspension is added to 100 mL of boiling water. The resulting paste is added to the pulverulent substances and the mixture is granulated, if necessary with the addition of water. The granulate is dried overnight at 35° C. forced through a sieve of 1.2 mm mesh width and compressed to form tablets of approximately 6 mm diameter which are concave on both sides.

Example 20

Tablets for chewing, each containing 75 mg of 1-oxo-2-(2,6-dioxopiperidin-3-yl)-4-aminoisoindoline, can be prepared in the following manner:

| Composition (for 1000 tablets) | |
|---|---|
| 1-oxo-2-(2,6-dioxo-piperidin-3-yl)-4-amino-isoindoline | 75.0 g |
| mannitol | 230.0 g |
| lactose | 150.0 g |
| talc | 21.0 g |
| glycine | 12.5 g |
| stearic acid | 10.0 g |
| saccharin | 1.5 g |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. 1-Oxo-2-(2,6-dioxopiperidin-3-yl)-4-aminoisoindoline, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

Example 21

Tablets, each containing 10 mg of 1-oxo-2-(2,6-dioxopiperidin-3-yl)-5-aminoisoindoline, can be prepared in the following manner:

| Composition (for 1000 tablets) | |
|---|---|
| 1-oxo-2-(2,6-dioxopiperidin-3-yl)-5-aminoisoindoline | 10.0 g |
| lactose | 328.5 g |
| corn starch | 17.5 g |
| polyethylene glycol 6000 | 5.0 g |
| talc | 25.0 g |

| Composition (for 1000 tablets) | |
|---|---|
| magnesium stearate | 4.0 g |
| demineralized water | q.s. |

The solid ingredients are first forced through a sieve of 0.6 mm mesh width. Then the active imide ingredient, lactose, talc, magnesium stearate and half of the starch are intimately mixed. The other half of the starch is suspended in 65 mL of water and this suspension is added to a boiling solution of the polyethylene glycol in 260 mL of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

Example 22

Gelatin dry-filled capsules, each containing 100 mg of 1-oxo-2-(2,6-dioxopiperidin-3-yl)-6-aminoisoindoline, can be prepared in the following manner:

| Composition (for 1000 capsules) | |
|---|---|
| 1-oxo-2-(2,6-dioxopiperidin-3-yl)-6-aminoisoindoline | 100.0 g |
| microcrystalline cellulose | 30.0 g |
| sodium lauryl sulfate | 2.0 g |
| magnesium stearate | 8.0 g |

The sodium lauryl sulfate is sieved into the 1-oxo-2-(2,6-dioxopiperidin-3-yl)-6-aminoisoindoline through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 mg each into size 0 (elongated) gelatin dry-fill capsules.

Example 23

A 0.2% injection or infusion solution can be prepared, for example, in the following manner:

| | |
|---|---|
| 1-oxo-2-(2,6-dioxopiperidin-3-yl)-7-aminoisoindoline | 5.0 g |
| sodium chloride | 22.5 g |
| phosphate buffer pH 7.4 | 300.0 g |
| demineralized water | to 2500.0 mL |

1-Oxo-2-(2,6-dioxopiperidin-3-yl)-7-aminoisoindoline is dissolved in 1000 mL of water and filtered through a microfilter. The buffer solution is added and the whole is made up to 2500 mL with water. To prepare dosage unit forms, portions of 1.0 or 2.5 mL each are introduced into glass ampoules (each containing respectively 2.0 or 5.0 mg of imide).

Example 24

Tablets, each containing 50 mg of 1-oxo-2-(2,6-dioxopiperidin-3-yl)-4,5,6,7-tetrafluoroisoindoline, can be prepared in the following manner:

| Constituents (for 1000 tablets) | |
|---|---|
| 1-oxo-2-(2,6-dioxopiperidin-3-yl)-4,5,6,7-tetrafluoroisoindoline | 50.0 g |
| lactose | 50.7 g |
| wheat starch | 7.5 g |
| polyethylene glycol 6000 | 5.0 g |
| talc | 5.0 g |
| magnesium stearate | 1.8 g |
| demineralized water | q.s. |

The solid ingredients are first forced through a sieve of 0.6 mm mesh width. The active ingredient, lactose, talc, magnesium stearate and half of the starch then are mixed. The other half of the starch is suspended in 40 mL of water and this suspension is added to a boiling solution of the polyethylene glycol in 100 mL of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

Example 25

Tablets, each containing 100 mg of 1-oxo-2-(2,6-dioxopiperidin-3-yl)-4,5,6,7-tetrachloroisoindoline, can be prepared in the following manner.

| Constituents (for 1000 tablets) | |
|---|---|
| 1-oxo-2-(2,6-dioxopiperidin-3-yl)-4,5,6,7-tetrachloroisoindoline | 100.0 g |
| lactose | 100.0 g |
| wheat starch | 47.0 g |
| magnesium stearate | 3.0 g |

All the solid ingredients are first forced through a sieve of 0.6 mm mesh width. The active ingredient, lactose, magnesium stearate and half of the starch then are mixed. The other half of the starch is suspended in 40 mL of water and this suspension is added to 100 mL of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

Example 26

Tablets for chewing, each containing 75 mg of 1-oxo-2-(2,6-dioxopiperidin-3-yl)-4,5,6,7-tetrafluoroisoindoline, can be prepared in the following manner:

| Composition (for 1000 tablets) | |
|---|---|
| 1-oxo-2-(2,6-dioxopiperidin-3-yl)-4,5,6,7-tetrafluoroisoindoline | 75.0 g |
| mannitol | 230.0 g |
| lactose | 150.0 g |
| talc | 21.0 g |
| glycine | 12.5 g |
| stearic acid | 10.0 g |

| Composition (for 1000 tablets) | |
|---|---|
| saccharin | 1.5 g |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. 1-Oxo-2-(2,6-dioxopiperidin-3-yl)-4,5,6,7-tetrafluoroisoindoline, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

Example 27

Tablets, each containing 10 mg of 1-oxo-2-(2,6-dioxopiperidin-3-yl)-4,5,6,7-tetramethylisoindoline, can be prepared in the following manner:

| Composition (for 1000 tablets) | |
|---|---|
| 1-oxo-2-(2,6-dioxopiperidin-3-yl)-4,5,6,7-tetramethylisoindoline | 10.0 g |
| lactose | 328.5 g |
| corn starch | 17.5 g |
| polyethylene glycol 6000 | 5.0 g |
| talc | 25.0 g |
| magnesium stearate | 4.0 g |
| demineralized water | q.s. |

The solid ingredients are first forced through a sieve of 0.6 mm mesh width. Then the active imide ingredient, lactose, talc, magnesium stearate and half of the starch are intimately mixed. The other half of the starch is suspended in 65 mL of water and this suspension is added to a boiling solution of the polyethylene glycol in 260 mL of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

Example 28

Gelatin dry-filled capsules, each containing 100 mg of 1-oxo-2-(2,6-dioxopiperidin-3-yl)-4,5,6,7-tetramethoxyisoindoline, can be prepared in the following manner:

| Composition (for 1000 capsules) | |
|---|---|
| 1-oxo-2-(2,6-dioxopiperidin-3-yl)-4,5,6,7-tetramethoxyisoindoline | 100.0 g |
| microcrystalline cellulose | 30.0 g |
| sodium lauryl sulfate | 2.0 g |
| magnesium stearate | 8.0 g |

The sodium lauryl sulfate is sieved into the 1-oxo-2-(2,6-dioxopiperidin-3-yl)-4,5,6,7-tetramethoxyisoindoline through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 mg each into size 0 (elongated) gelatin dry-fill capsules.

Example 30

A 0.2% injection or infusion solution can be prepared, for example, in the following manner:

| | |
|---|---|
| 1-oxo-2-(2,6-dioxopiperidin-3-yl)-4,5,6,7-tetrafluoroisoindoline | 5.0 g |
| sodium chloride | 22.5 g |
| phosphate buffer pH 7.4 | 300.0 g |
| demineralized water | to 2500.0 mL |

1-Oxo-2-(2,6-dioxopiperidin-3-yl)-4,5,6,7-tetrafluoroisoindoline is dissolved in 1000 mL of water and filtered through a microfilter. The buffer solution is added and the whole is made up to 2500 mL with water. To prepare dosage unit forms, portions of 1.0 or 2.5 mL each are introduced into glass ampoules (each containing respectively 2.0 or 5.0 mg of imide).

Example 31

Tablets, each containing 50 mg of 1-oxo-2-(2,6-dioxo-3-methylpiperidin-3-yl)-4,5,6,7-tetrafluoroisoindoline, can be prepared in the following manner:

| Constituents (for 1000 tablets) | |
|---|---|
| 1-oxo-2-(2,6-dioxo-3-methylpiperidin-3-yl)-4,5,6,7-tetrafluoroisoindoline | 50.0 g |
| lactose | 50.7 g |
| wheat starch | 7.5 g |
| polyethylene glycol 6000 | 5.0 g |
| talc | 5.0 g |
| magnesium stearate | 1.8 g |
| demineralized water | q.s. |

The solid ingredients are first forced through a sieve of 0.6 mm mesh width. The active ingredient, lactose, talc, magnesium stearate and half of the starch then are mixed. The other half of the starch is suspended in 40 mL of water and this suspension is added to a boiling solution of the polyethylene glycol in 100 mL of water. The resulting paste is added to the pulverulent substances and the mixture is granulated, if necessary with the addition of water. The granulate is dried overnight at 35° C. forced through a sieve of 1.2 mm mesh width and compressed to form tablets of approximately 6 mm diameter which are concave on both sides.

Example 32

Tablets, each containing 100 mg of 1-oxo-2-(2,6-dioxopiperidin-3-yl)-4-aminoisoindoline, can be prepared in the following manner:

| Constituents (for 1000 tablets) | |
|---|---|
| 1-oxo-2-(2,6-dioxopiperidin-3-yl)-4-aminoisoindoline | 100.0 g |

-continued

| Constituents (for 1000 tablets) | |
|---|---|
| lactose | 100.0 g |
| wheat starch | 47.0 g |
| magnesium stearate | 3.0 g |

All the solid ingredients are first forced through a sieve of 0.6 mm mesh width. The active ingredient, lactose, magnesium stearate and half of the starch then are mixed. The other half of the starch is suspended in 40 mL of water and this suspension is added to 100 mL of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 min diameter which are concave on both sides.

Example 33

Tablets for chewing, each containing 75 mg of 2-(2,6-dioxo-3-methylpiperidin-3-yl)-4-aminophthalimide, can be prepared in the following manner:

| Composition (for 1000 tablets) | |
|---|---|
| 2-(2,6-dioxo-3-methylpiperidin-3-yl)-4-aminophthalimide | 75.0 g |
| mannitol | 230.0 g |
| lactose | 150.0 g |
| talc | 21.0 g |
| glycine | 12.5 g |
| stearic acid | 10.0 g |
| saccharin | 1.5 g |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. 2-(2,6-Dioxo-3-methylpiperidin-3-yl)-4-aminophthalimide, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

Example 34

Tablets, each containing 10 mg of 2-(2,6-dioxoethylpiperidin-3-yl)-4-aminophthalimide, can be prepared in the following manner:

| Composition (for 1000 tablets) | |
|---|---|
| 2-(2,6-dioxoethylpiperidin-3-yl)-4-aminophthalimide | 10.0 g |
| lactose | 328.5 g |
| corn starch | 17.5 g |
| polyethylene glycol 6000 | 5.0 g |
| talc | 25.0 g |
| magnesium stearate | 4.0 g |
| demineralized water | q.s. |

The solid ingredients are first forced through a sieve of 0.6 mm mesh width. Then the active imide ingredient, lactose, talc, magnesium stearate and half of the starch are intimately mixed. The other half of the starch is suspended in 65 mL of water and this suspension is added to a boiling solution of the polyethylene glycol in 260 mL of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

Example 35

Gelatin dry-filled capsules, each containing 100 mg of 1-oxo-2-(2,6-dioxo-3-methylpiperidin-3-yl)-4,5,6,7-tetrafluoroisoindoline, can be prepared in the following manner:

| Composition (for 1000 capsules) | |
|---|---|
| 1-oxo-2-(2,6-dioxo-3-methylpiperidin-3-yl)-4,5,6,7-tetrafluoroisoindoline | 100.0 g |
| microcrystalline cellulose | 30.0 g |
| sodium lauryl sulfate | 2.0 g |
| magnesium stearate | 8.0 g |

The sodium lauryl sulfate is sieved into the 1-oxo-2-(2,6-dioxo-3-Methylpiperidin-3-yl)-4,5,6,7-tetrafluoroisoindoline through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 mg each into size 0 (elongated) gelatin dry-fill capsules.

Example 36

A 0.2% injection or infusion solution can be prepared, for example, in the following manner:

| | |
|---|---|
| 1-oxo-2-(2,6-dioxo-3-methylpiperidin-3-yl)-4,5,6,7-tetrafluoroisoindoline | 5.0 g |
| sodium chloride | 22.5 g |
| phosphate buffer pH 7.4 | 300.0 g |
| demineralized water | to 2500.0 mL |

1-Oxo-2-(2,6-dioxo-3-methylpiperidin-3-yl)-4,5,6,7-tetrafluoroisoindoline is dissolved in 1000 mL of water and filtered through a microfilter. The buffer solution is added and the whole is made up to 2500 mL with water. To prepare dosage unit forms, portions of 1.0 or 2.5 mL each are introduced into glass ampoules (each containing respectively 2.0 or 5.0 mg of imide).

The invention claimed is:

1. A unit dosage form comprising an amount of a compound of the formula:

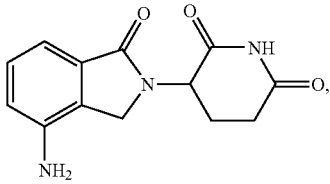

or an acid addition salt thereof, and a pharmaceutically acceptable carrier, diluent, or excipient, wherein the amount is from 1 mg to 100 mg.

2. The unit dosage form of claim 1, which is a single unit dosage form.

3. The unit dosage form of claim 1, which is adopted for oral administration.

4. The unit dosage form of claim 3, which is in the form of a tablet.

5. The unit dosage form of claim 3, which is in the form of a capsule.

6. A compound of the formula:

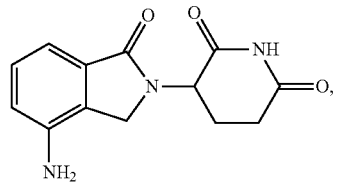

or an acid addition salt thereof.

* * * * *